United States Patent
Kitamura

(10) Patent No.: US 11,929,174 B2
(45) Date of Patent: Mar. 12, 2024

(54) MACHINE LEARNING METHOD AND APPARATUS, PROGRAM, LEARNED MODEL, AND DISCRIMINATION APPARATUS USING MULTILAYER NEURAL NETWORK

(71) Applicant: FUJIFILM Corporation, Tokyo (JP)

(72) Inventor: Yoshiro Kitamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 890 days.

(21) Appl. No.: 16/985,237

(22) Filed: Aug. 5, 2020

(65) Prior Publication Data

US 2020/0364570 A1 Nov. 19, 2020

Related U.S. Application Data

(63) Continuation of application No. PCT/JP2019/007050, filed on Feb. 25, 2019.

(30) Foreign Application Priority Data

Feb. 28, 2018 (JP) ................. 2018-035355

(51) Int. Cl.
  *G06N 3/08* (2023.01)
  *G06F 18/21* (2023.01)
  (Continued)

(52) U.S. Cl.
  CPC ........... *G16H 50/20* (2018.01); *G06F 18/217* (2023.01); *G06F 18/2431* (2023.01);
  (Continued)

(58) Field of Classification Search
  CPC ............................... G06N 3/045; G06N 3/08
  See application file for complete search history.

(56) References Cited

U.S. PATENT DOCUMENTS

2017/0364826 A1  12/2017  Mitarai

FOREIGN PATENT DOCUMENTS

| JP | H0962644 | 3/1997 |
| JP | 2012014617 | 1/2012 |

(Continued)

OTHER PUBLICATIONS

Qquab et al. "Learning and Transferring Mid-Level Image Representations using Convolutional Neural Networks", IEEE CVPR, 2014, pp. 1717-1724.*

(Continued)

*Primary Examiner* — Li Wu Chang
(74) *Attorney, Agent, or Firm* — JCIPRNET

(57) ABSTRACT

A machine learning method and an apparatus, a program, a learned model, and a discrimination apparatus capable of controlling a calculation amount by learning a new task without changing output performance for an existing task in a learned network are provided. A machine learning method according to one aspect of the present disclosure includes a step of adding a new feature amount to at least one intermediate layer included in a learned first neural network that has learned a task of performing first class classification, a step of generating a second neural network having a structure in which a network structure of a calculation path of an existing feature amount of the first neural network is maintained and a new feature amount of a subsequent layer is calculated by performing processing of convolving each of the existing feature amount and the new feature amount, and a step of causing the second neural network to acquire a (Continued)

processing function of performing second class classification by performing learning of the second neural network using a set of learning data corresponding to the second class classification.

16 Claims, 13 Drawing Sheets

(51) Int. Cl.
*G06F 18/2431* (2023.01)
*G06N 3/045* (2023.01)
*G06V 10/44* (2022.01)
*G06V 10/764* (2022.01)
*G06V 10/82* (2022.01)
*G16H 50/20* (2018.01)
*G16H 30/40* (2018.01)

(52) U.S. Cl.
CPC .............. *G06N 3/045* (2023.01); *G06N 3/08* (2013.01); *G06V 10/454* (2022.01); *G06V 10/764* (2022.01); *G06V 10/82* (2022.01); *G06V 2201/031* (2022.01); *G16H 30/40* (2018.01)

(56) References Cited

FOREIGN PATENT DOCUMENTS

| JP | 2017182320 | 10/2017 |
| JP | 2017224156 | 12/2017 |

OTHER PUBLICATIONS

Olaf Ronneberger et al., "U-Net: Convolutional Networks for Biomedical Image Segmentation", Computer Science Department and BIOSS Centre for Biological Signalling Studies, University of Freiburg, Germany, May 18, 2015, pp. 1-8.

Yaroslav Ganin et al., "Unsupervised Domain Adaptation by Backpropagation", 32 nd International Conference on Machine Learning, Feb. 27, 2015, pp. 1-11.

"International Search Report (Form PCT/ISA/210) of PCT/JP2019/007050," dated Apr. 23, 2019, with English translation thereof, pp. 1-4.

"Written Opinion of the International Searching Authority (Form PCT/ISA/237) of PCT/JP2019/007050," dated Apr. 23, 2019, with English translation thereof, pp. 1-7.

\* cited by examiner

MACHINE LEARNING METHOD AND APPARATUS, PROGRAM, LEARNED MODEL, AND DISCRIMINATION APPARATUS USING MULTILAYER NEURAL NETWORK

CROSS-REFERENCE TO RELATED APPLICATIONS

The present application is a Continuation of PCT International Application No. PCT/JP2019/007050 filed on Feb. 25, 2019 claiming priority under 35 U.S.C § 119(a) to Japanese Patent Application No. 2018-035355 filed on Feb. 28, 2018. Each of the above applications is hereby expressly incorporated by reference, in its entirety, into the present application.

BACKGROUND OF THE INVENTION

1. Field of the Invention

The present invention relates to a machine learning method and apparatus, a program, a learned model, and a discrimination apparatus and particularly, to a deep learning technology for implementing a task such as image recognition using a multilayer neural network.

2. Description of the Related Art

In recent years, technologies for recognizing an image using a multilayer neural network have been actively developed. For example, in the medical field, the importance of medical image diagnosis such as endoscopic diagnosis, ultrasound diagnosis, X-ray image diagnosis, and computerized tomography (CT) image diagnosis is high, and automation of the medical image diagnosis uses image recognition methods using machine learning.

In Olaf Ronneberger, Philipp Fischer, Thomas Brox.: U-Net: Convolutional Networks for Biomedical Image Segmentation: Medical Image Computing and Computer-Assisted Intervention (MICCAI), Springer, LNCS, Vol. 9351: 234-241, 2015, arXiv:1505.04597 [cs.CV], a U-shaped network called a "U-Net structure" is suggested as a neural network for performing medical image segmentation. In the expression of "U-Net", "Net" is a simple expression of a "network", and the "network" means a neural network. The U-Net structure has a structure including an encoder part and a decoder part and is configured to include downsampling processing of decreasing the number of pixels and deconvolution (upsampling) processing of increasing the number of pixels in a pooling operation subsequent to convolution (convolutional) processing.

In an end-to-end segmentation framework in deep learning, a region of a desired object is extracted by learning a pair of an input image and a label image having the same size.

One significant factor in successful deep learning is learning a large amount of learning data. However, data of medical images or the like is rare, and it is difficult to prepare a large amount of data. Therefore, a technique called "transfer learning" is used (JP2017-224156A). Transfer learning is learning another problem (for example, class classification for medical images) using a part of a network that has once learned in a field where a large amount of data such as photographic images can be used. Optimization of the network to solve a new problem using a parameter of the learned network as an initial value is called fine tuning. Optimization may also be performed by fixing and not changing a parameter of a network on a low layer side at all in the learned network and switching only a layer (particularly, the last layer) in a rear stage.

SUMMARY OF THE INVENTION

For example, in the case of performing a class classification task of extracting a region of a specific organ such as a heart, a liver, or a kidney from a CT image, it is considered that an independent neural network learns for each individual organ to be extracted and the learned network is used in actual discrimination processing.

However, in the case of a form of using the independent learned network of a single task for each organ, it is necessary to perform calculation corresponding to the number of organs in a case where a plurality of types of organs to be set as an extraction target are present.

Meanwhile, in a case where a neural network corresponding to a multiclass classification task is originally constructed, a plurality of tasks share an intermediate feature map, and multiple organs can be extracted at the same time with a small calculation amount. However, a request for adding a classification function for another new organ group may be made after a network for classifying a desired organ group is completed. That is, recognition performance may be low for only specific one or a plurality of organs among multiple organs to be discriminated, and the learned (existing) network may be desired to re-learn. At this point, in a case where re-learning is executed by simply adding learning data including a label image of a new class, output of a task of classifying an organ related to an existing classification target other than the specific organ for which the recognition performance is desired to be enhanced is also changed, and maintainability deteriorates. A system that can add processing performance for a new task without changing output performance related to an existing task in a learned network is desired.

The above object is an object that is not limited to a network for solving a problem of medical image segmentation and is common to a network for performing a multiclass classification task.

The present invention is conceived in view of such a matter, and one aim thereof is to provide a machine learning method, an apparatus, and a program capable of learning a new task without changing output performance for an existing task in a learned network and furthermore, controlling a calculation amount. Another aim of the present invention is to provide a learned model that acquires processing performance for a new task in addition to an existing task, and a discrimination apparatus using the learned model.

In order to solve the object, the following invention aspects are provided.

A machine learning method according to Aspect 1 is a machine learning method of learning of a second neural network for performing a task of second class classification including a different class from first class classification in addition to a task of the first class classification using a first neural network that is a learned hierarchical neural network which has learned the task of performing the first class classification by machine learning, the method comprising a step of adding a new feature amount to at least one intermediate layer included in the first neural network, a step of generating a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and a step of causing the second neural network to acquire a processing function of performing the second class classification by performing learning of the second neural network using a set of learning data in which an answer label corresponding to the second class classification is assigned.

The "neural network" is a mathematical model of information processing that simulates the mechanism of the nervous system. Processing using the neural network can be implemented using a computer. The neural network may be configured as a program module. In the present specification, the neural network may be simply referred to as the "network".

Here, "adding the new feature amount" refers to addition of a feature extraction filter for calculating or generating a feature map of a new channel for an image or a feature map that is data input into a layer. A feature amount calculated (extracted) using the filter is referred to as the feature map. The feature map is calculated for each filter.

According to Aspect 1, the second neural network to which the processing function for the task of the second class classification is added without changing output performance of the learned first neural network for the task of the first class classification can be obtained.

According to Aspect 1, a part of the feature amounts (existing feature amount) is shared between the first neural network and the second neural network. Thus, duplicate calculation of the shared feature amount is not necessary. Accordingly, a calculation amount is controlled, and the execution speed of calculation can be maintained at a high speed.

A machine learning method according to Aspect 2 is a machine learning method comprising a step of causing a first neural network that is a hierarchical neural network to acquire a processing function of performing first class classification by performing first machine learning regarding the first neural network using a first learning data set in which an answer label corresponding to the first class classification is assigned, a step of adding a new feature amount to at least one intermediate layer included in the learned first neural network that has acquired the processing function of performing the first class classification, a step of generating a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and a step of causing the second neural network to acquire a processing function of performing second class classification by performing second machine learning regarding the second neural network using a second learning data set in which an answer label corresponding to the second class classification including a different class from the first class classification is assigned.

According to Aspect 2, the learned first neural network for the task of the first class classification can be obtained, and the second neural network to which the processing function for the task of the second class classification is added without changing the output performance of the learned first neural network for the task of the first class classification can be obtained.

According to Aspect 2, a part of the feature amounts (existing feature amount) is shared between the first neural network and the second neural network. Thus, duplicate calculation of the shared feature amount is not necessary. Accordingly, a calculation amount is controlled, and the execution speed of calculation can be maintained at a high speed.

Aspect 3 is a machine learning method in which in the machine learning method of Aspect 1 or Aspect 2, in a case of learning of the second neural network, a parameter of the calculation path of the existing feature amount present in the learned first neural network is set to be invariable.

The "parameter" includes a filter coefficient (connection weight) of the filter used in processing of each layer, a bias of a node, and the like in the neural network.

Aspect 4 is a machine learning method in which in the machine learning method of any one aspect of Aspect 1 to Aspect 3, the first neural network has a network structure in which a downsampling network functioning as an encoder and an upsampling network functioning as a decoder are combined, and the new feature amount is added to the upsampling network out of the downsampling network and the upsampling network.

Aspect 5 is a machine learning method in which in the machine learning method of Aspect 4, the first neural network has a U-Net structure.

A learned model according to Aspect 6 is a learned model having acquired a processing function of performing tasks of first class classification and second class classification through learning of the second neural network by performing the machine learning method of any one aspect of Aspect 1 to Aspect 5.

A discrimination apparatus according to Aspect 7 is a discrimination apparatus comprising a learned model having acquired a processing function of performing tasks of first class classification and second class classification through learning of the second neural network by performing the machine learning method of any one aspect of Aspect 1 to Aspect 5.

The term "discrimination" includes the concepts of recognition, identification, inference, estimation, prediction, supposition, detection, region extraction, and the like. The term "apparatus" includes the concept of a "system".

A program according to Aspect 8 is a program causing a computer to execute processing of first class classification and second class classification using a learned model having acquired a processing function of performing tasks of first class classification and second class classification through learning of the second neural network by performing the machine learning method of any one aspect of Aspect 1 to Aspect 5.

A program according to Aspect 9 is a program causing a computer to execute the machine learning method of any one aspect of Aspect 1 to Aspect 5.

A machine learning apparatus according to Aspect 10 is a machine learning apparatus performing learning of a second neural network for performing a task of second class classification including a different class from first class classification in addition to a task of the first class classification using a first neural network that is a learned hierarchical neural network which has learned the task of performing the first class classification by machine learning, the apparatus comprising a feature amount addition processing unit that adds a new feature amount to at least one intermediate layer included in the first neural network, a network generation unit that generates a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and a learning processing unit that causes the second neural network to acquire a processing function of performing the second class classification by performing learning of the second neural network using a set of learning data in which an answer label corresponding to the second class classification is assigned.

A machine learning apparatus according to Aspect 11 is a machine learning apparatus comprising a first learning processing unit that causes a first neural network which is a hierarchical neural network to acquire a processing function of performing first class classification by performing first machine learning regarding the first neural network using a first learning data set in which an answer label corresponding to the first class classification is assigned, a feature amount addition processing unit that adds a new feature amount to at least one intermediate layer included in the learned first neural network which has acquired the processing function of performing the first class classification, a network generation unit that generates a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and a second learning processing unit that causes the second neural network to acquire a processing function of performing second class classification by performing second machine learning regarding the second neural network using a second learning data set in which an answer label corresponding to the second class classification including a different class from the first class classification is assigned.

In the machine learning apparatus of Aspect 10 or Aspect 11, the same matters as the matters specified in Aspect 3 to Aspect 5 can be appropriately combined.

A machine learning apparatus according to another aspect of the present invention is a machine learning apparatus including at least one processor that performs processing of learning of a second neural network for performing a task of second class classification including a different class from first class classification in addition to a task of the first class classification using a first neural network that is a learned hierarchical neural network which has learned the task of performing the first class classification by machine learning, the processor performing feature amount addition processing of adding a new feature amount to at least one intermediate layer included in the first neural network, network generation processing of generating a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and learning processing of causing the second neural network to acquire a processing function of performing the second class classification by performing learning of the second neural network using a set of learning data in which an answer label corresponding to the second class classification is assigned.

A machine learning apparatus according to another aspect of the present invention is a machine learning apparatus including at least one processor, the processor performing first learning processing of causing a first neural network which is a hierarchical neural network to acquire a processing function of performing first class classification by performing first machine learning regarding the first neural network using a first learning data set in which an answer label corresponding to the first class classification is assigned, feature amount addition processing of adding a new feature amount to at least one intermediate layer included in the learned first neural network which has acquired the processing function of performing the first class classification, network generation processing of generating a second neural network having a structure for maintaining a structure of the first neural network without connecting the new feature amount with respect to a calculation path of an existing feature amount present in the first neural network and calculating a new feature amount to be added in a subsequent layer by performing processing of convolving each of the existing feature amount and the new feature amount with respect to a calculation path of the new feature amount, and second learning processing of causing the second neural network to acquire a processing function of performing second class classification by performing second machine learning regarding the second neural network using a second learning data set in which an answer label corresponding to the second class classification including a different class from the first class classification is assigned.

According to the present invention, a new neural network to which a function of a new task is added without changing output performance for an existing task in a learned existing neural network can be provided.

According to the present invention, a part of feature amounts is shared between the existing neural network and the new neural network to which the function is added. Thus, the calculation amount is controlled, and the execution speed of calculation can be maintained at a high speed, compared to those in a configuration of using an independent neural network of a single task for each classification target.

DESCRIPTION OF THE PREFERRED EMBODIMENTS

Hereinafter, preferred embodiments of the present invention will be described in detail in accordance with the appended drawings.

A machine learning method according to one embodiment of the present invention is a learning method of a neural network for solving a multiclass classification problem. A task of segmenting a plurality of organs from a CT image will be illustrated as one example of the multiclass classification problem.

<Example of Segmentation of Multiple Organs>

Figure 1:
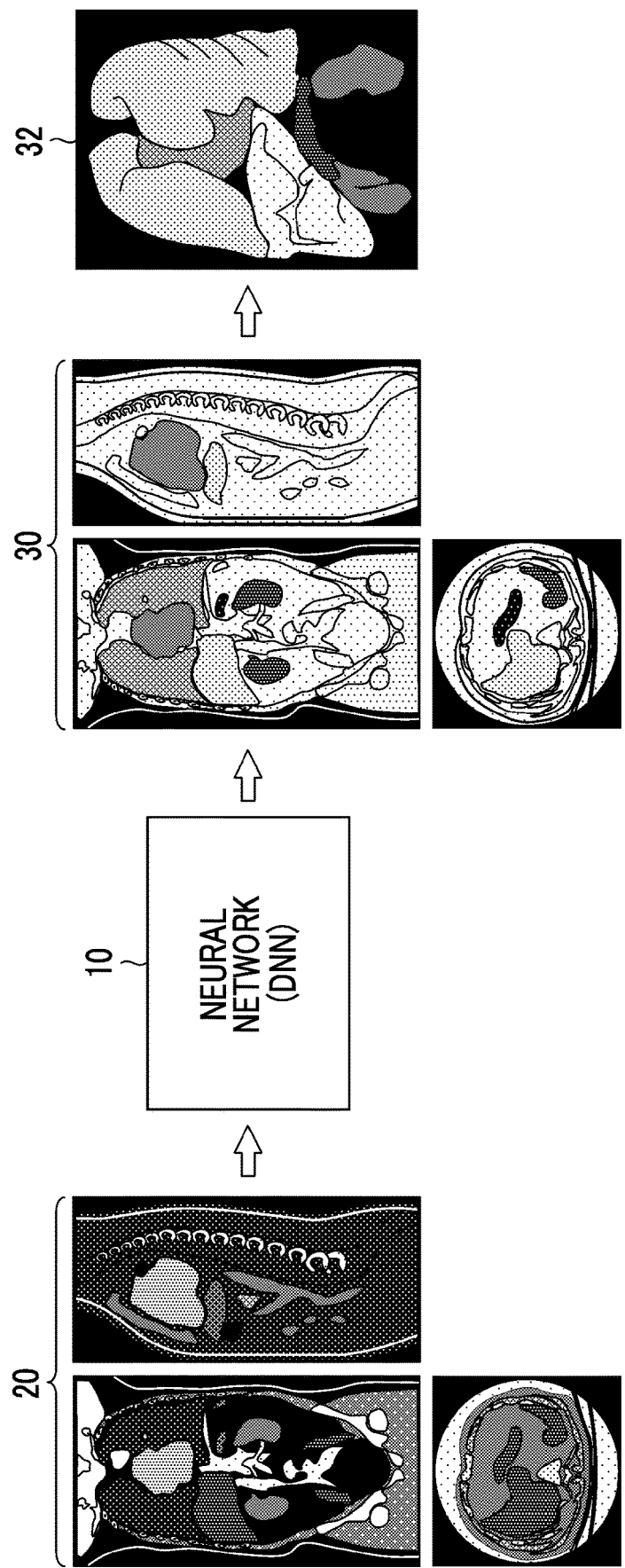
FIG. 1 is a diagram illustrating a processing example of segmentation of multiple organs for a CT image.

FIG. 1 is a diagram illustrating a processing example of segmentation of multiple organs for the CT image. A neural network 10 for processing segmentation is a hierarchical neural network classified as a deep neural network (DNN). The neural network 10 is a neural network including a convolutional layer that performs convolutional calculation. Various farms may be present as a layer structure of the neural network 10. It is preferable that the neural network 10 has an encoder-decoder structure in which an encoder part and a decoder part are combined. For example, a U-Net structure is one example of a preferred architecture of the neural network 10 for solving the problem of segmentation.

The neural network 10 is a learned model that acquires a segmentation function for multiple organs by applying a machine learning method, described later. The learned model may be referred to as a program module.

Input data of the neural network 10 of the present example is a CT image 20. For example, the CT image 20 may be a multislice CT image. An aggregate of multislice CT images corresponds to three-dimensional image data.

Segmentation of the multislice CT image is a task of assigning a label indicating which organ corresponds to each voxel and displaying each label in a different color. For example, in the case of performing segmentation for five types of organs including a lung, a heart, a liver, a kidney, and a pancreas, a problem of discriminating an organ to which one voxel constituting the image belongs, that is, estimating a class for which certainty (likelihood) of belonging to the class is the highest among six types of classes including the five types of organs plus "others" for each voxel, is solved.

In a case where the CT image 20 is input into the neural network 10, the neural network 10 discriminates the class to which each voxel of the CT image 20 belongs and outputs a segmented CT image 30 that is divided into regions for each organ.

Based on data of the segmented CT image 30 output by the neural network 10, for example, the three-dimensional shape of each organ can be extracted by volume rendering, and a volume rendering image 32 of each organ can be obtained.

<Description of U-Net Structure>

Figure 2:
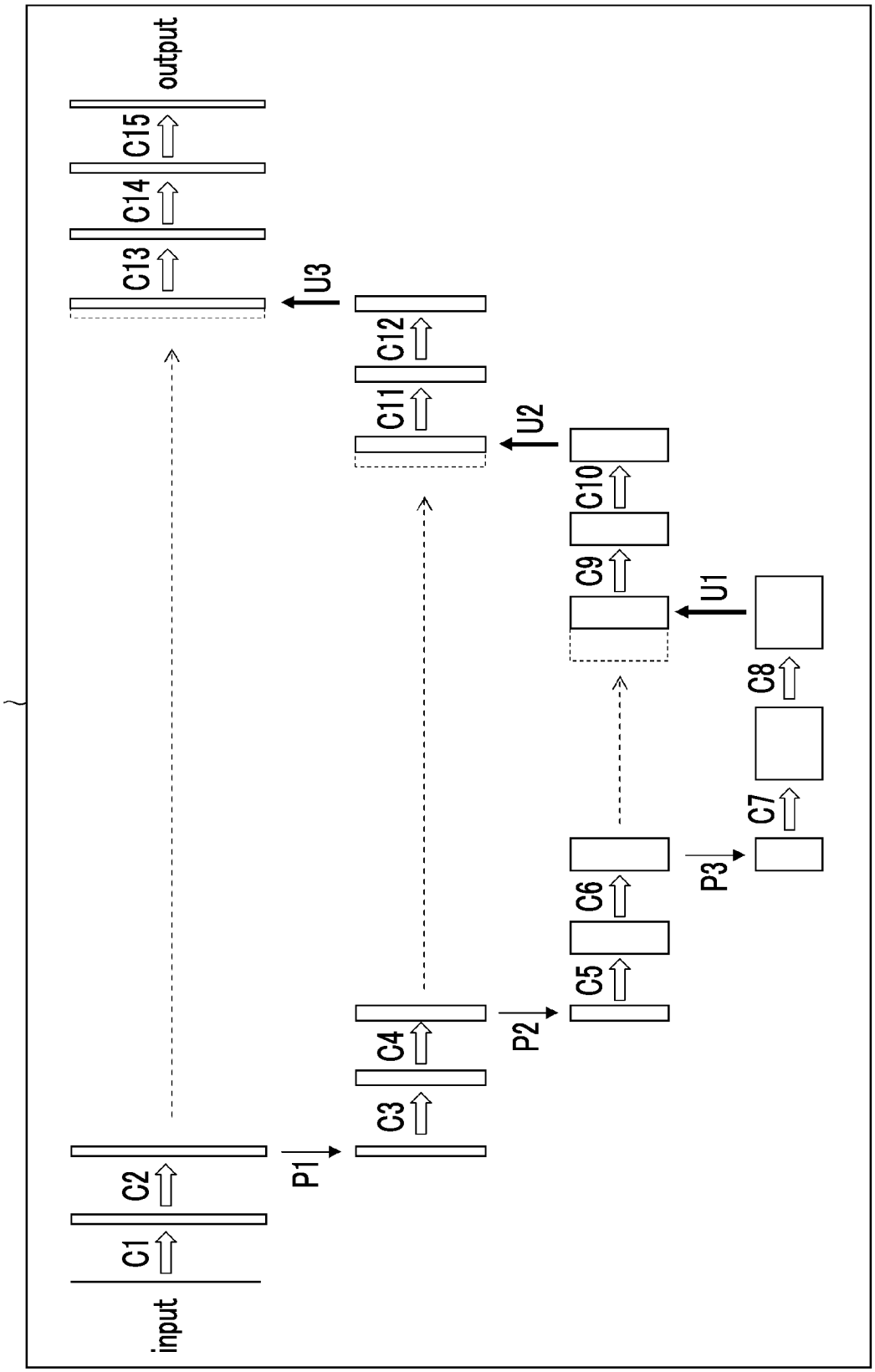
FIG. 2 is a conceptual diagram illustrating an example of a neural network having a U-net structure.

A neural network having the U-net structure will be simply described. FIG. 2 is a conceptual diagram illustrating an example of the neural network having the U-net structure. In FIG. 2, each of arrows denoted by reference signs C1, C2, . . . , C15 represents a "convolutional layer". Each of arrows denoted by reference signs P1, P2, and P3 represents a "pooling layer". Arrows denoted by reference signs U1, U2, and U3 represent "unpooling layers". Each of the convolutional layers C9 to C15 corresponds to a "deconvolution layer".

Rectangles illustrated on an input side and/or an output side of each layer represent a set of feature maps. The length of the rectangle in a vertical direction represent the size (number of pixels) of the feature map, and the width of the rectangle in a horizontal direction represents the number of channels.

In the case of a network structure of a neural network 10A illustrated in FIG. 2, a first half part including the convolutional layers C1 and C2, the pooling layer P1, the convolutional layers C3 and C4, the pooling layer P2, the convolutional layers C5 and C6, the pooling layer P3, and the convolutional layers C7 and C8 from the input side corresponds to an encoder part. The sub-network of the encoder part is referred to as a downsampling network.

In FIG. 2, a second half part including the unpooling layer U1, the convolutional layers C9 and C10, the unpooling layer U2, the convolutional layers C11 and C12, the unpooling layer U3, and the convolutional layers C13, C14, and C15 corresponds to a decoder part. The convolutional layer C15 in the last stage may be a "1×1 convolutional layer" using a 1×1 filter. The sub-network of the decoder part is referred to as an upsampling network.

In FIG. 2, broken line arrows indicate that processing of combining feature maps of the encoder part and the decoder part having corresponding resolution is performed. In the decoder part, a set of feature maps illustrated by broken line rectangles indicates that the feature maps of the encoder part are copied. While illustration is not provided in FIG. 2, the feature maps of the encoder part may be cropped and then copied in order to equalize the resolution of the feature maps in the case of combining the feature maps.

<Summary of Machine Learning Method According to First Embodiment>

Organs to be set as a classification target are set to four types including a heart, a liver, a kidney, and a pancreas for simplification of description. In addition, a two-dimensional image will be described as an example instead of three-dimensional data. A "pixel" in the two-dimensional image corresponds to the "voxel" in the three-dimensional image, and description related to the two-dimensional image can be understood by extending the description to the three-dimensional image.

In a machine learning method according to a first embodiment, in order to obtain a discriminator that segments four types of organs including a heart, a liver, a kidney, and a pancreas, first, a neural network that has learned a segmentation function for three types of organs including the heart, the liver, and the kidney as an initial organ set is completed. Based on assumption that this learned neural network already exists, re-learning is performed in order to add a new segmentation function for the pancreas by using the learned (existing) neural network. The term "re-learning" includes concepts of transfer learning and additional learning.

In the machine learning method according to the first embodiment, in the case of performing the re-learning of the network to classify a new class using the existing neural network, a neural network having a structure in which a new feature amount is added to an intermediate layer in the existing neural network and a new feature amount in a subsequent layer is calculated by convolving each of an existing feature amount and the added new feature amount is generated.

In addition, in the case of performing the re-learning, a parameter is not updated for the existing feature amount originally included in the existing neural network. That is, for a calculation path of the existing feature amount present in the existing neural network, the structure of the existing neural network is maintained without connecting the new feature amount, and a learned parameter is also set to be invariable. This means that the new feature amount is not involved in calculation of the existing feature amount. The parameter of a part calculating the added new feature amount is optimized by the re-learning.

The neural network for classifying the initial organ set is referred to as a first neural network. The learned first neural network is referred to as an "existing neural network" or an "existing module". The neural network that has re-learned by adding the new feature amount to the existing neural network is referred to as a second neural network. The second neural network to which the classification function for the new class is added may be referred to as a "new module".

<Procedure of Learning of Neural Network>

Figure 3:
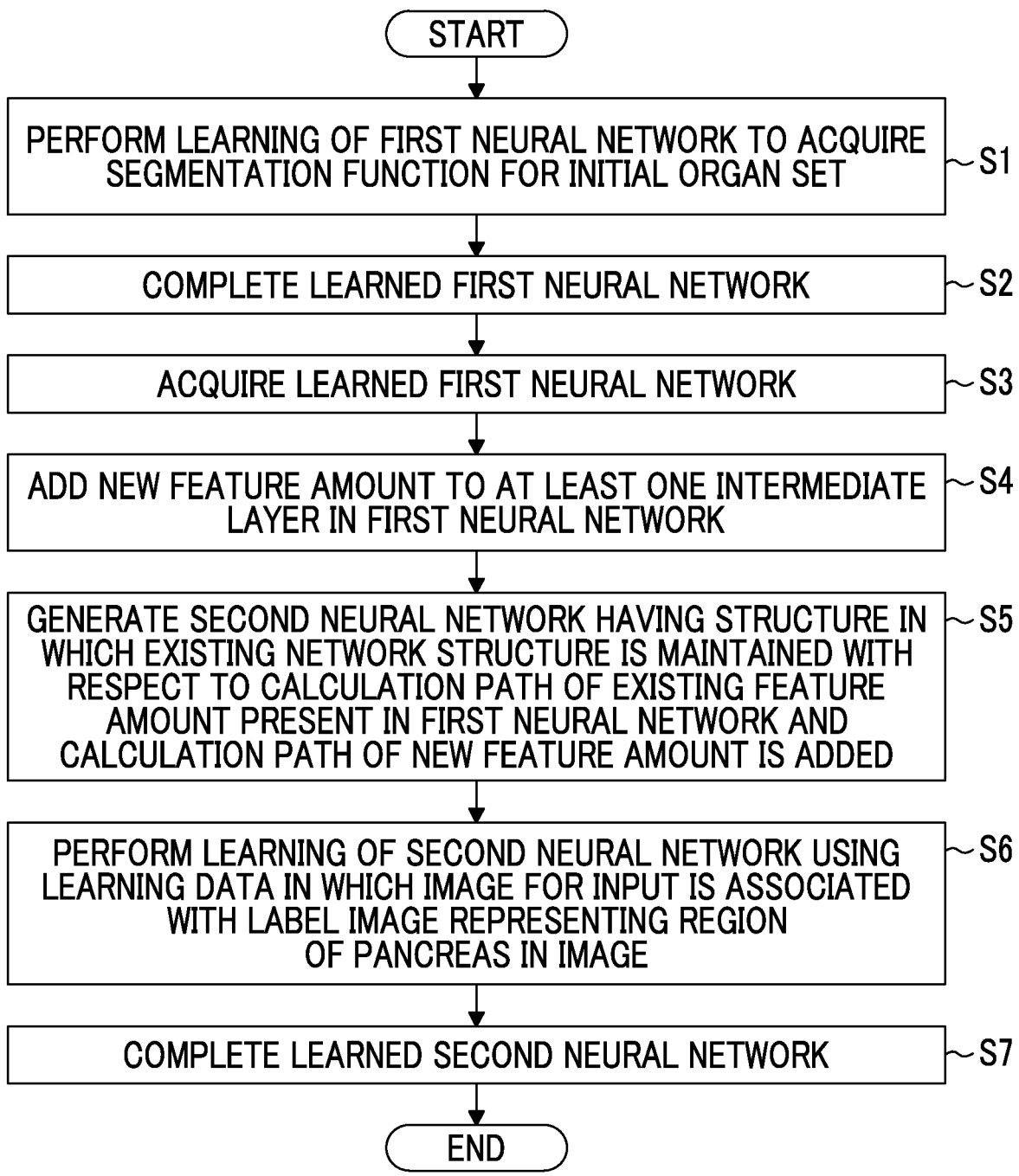
FIG. 3 is a flowchart illustrating a procedure of a machine learning method according to a first embodiment.

FIG. 3 is a flowchart illustrating a procedure of the machine learning method according to the first embodiment. Each step of the flowchart illustrated in FIG. 3 is executed by a machine learning apparatus configured by means of a computer. The computer may function as the machine learning apparatus by executing a program. The computer comprises a central processing unit (CPU) and a memory. The computer may include a graphics processing unit (GPU). Hereinafter, an information processing apparatus performing learning processing for the neural network will be referred to as the "machine learning apparatus". The term "machine learning apparatus" may be replaced with the term "information processing apparatus", "data processing apparatus", "signal processing apparatus", "image processing apparatus", or the like.

In step S1, the machine learning apparatus performs learning of the first neural network to acquire the segmentation function for the initial organ set. For example, the initial organ set can be set as three types of the heart, the liver, and the kidney. The organs included in the initial organ set may be appropriately selected and set in accordance with an aim.

In a first learning step of step S1, processing of optimizing the parameter of the first neural network is performed in accordance with an algorithm of an error backpropagation method (backpropagation) by applying a method of supervised learning using a first learning data set. The first learning data set is a collection of learning data in which an image for input is associated with a label image to which an answer label of each class of the heart, the liver, and the kidney corresponding to the image is assigned. The machine learning apparatus repeats processing of updating the parameter in units of minibatches.

The machine learning apparatus repeats the learning processing until a learning finish condition is satisfied. The learning finish condition may be set based on a value of an error between an output of a prediction result and a supervisory signal or may be set based on the number of updates of the parameter. As a method based on the value of the error, for example, the learning finish condition may be such that the error falls within a prescribed range. As a method based on the number of updates, for example, the learning finish condition may be such that the number of updates reaches a prescribed number.

In step S2, the machine learning apparatus finishes first learning processing and completes the learned first neural network. That is, the machine learning apparatus determines the learning finish condition and, in a case where the learning finish condition is satisfied, finishes the first learning processing and decides the parameter of the first neural network.

Accordingly, the learned first neural network that has learned the function of segmenting three organs can be obtained. The learned first neural network can be used as a discriminator that segments three organs.

Next, it is required to newly add a segmentation function for the pancreas as an organ not included in the initial organ set. Meanwhile, a constraint of not changing the output related to the organs included in the initial learning set is set. The reason is that the performance of the first neural network for discriminating the initial organ set is already checked as satisfying necessary performance by performance evaluation and the first neural network is completed as a discriminator discriminating three organs belonging to the initial organ set. The term discriminator may be referred to as a "discrimination apparatus" or a "discrimination module".

In the machine learning method according to the present embodiment, in order to newly implement the segmentation function for the pancreas without changing the output performance of the segmentation function related to the initial organ set, the re-learning including steps of learning using a partial change in network and new learning data is performed in order to implement the segmentation function for the pancreas using the learned first neural network (step S3 to step S7).

In step S3, the machine learning apparatus acquires the learned first neural network.

In step S4, the machine learning apparatus adds the new feature amount to at least one intermediate layer in the first neural network. The added new feature amount refers to a feature extraction filter for extracting a new feature. The number of new filters added to one layer is not limited to one and may be plural.

The new feature amount is added to each layer after a specific intermediate layer in order to use a calculation result (feature map) of a channel of the new feature amount added to the specific intermediate layer in calculation of the new feature amount in each layer after the subsequent layer.

In a network structure having consecutive convolutional layers, it is considered that a shallow layer close to the input side learns a common feature amount such as an edge of the image regardless of the class to be classified. As a layer is closer to an output layer, it is considered that the layer learns a feature amount specific to the feature of the class to be classified. Accordingly, it is preferable that the new feature amount is added to at least a layer close to the output. The new feature amount may be added to only the layer close to the output. The shallow layer propagates information sufficient for discriminating the new class without adding the new feature amount thereto.

The feature of the new class cannot be sufficiently learned using only the existing feature amount originally present in the first neural network. Thus, the new feature amount is added to the second half part of the network. For example, in the case of the U-Net structure, the new feature amount is not added to the downsampling network of the first half, and the new feature amount is added to the upsampling network of the second half.

In step S5, the machine learning apparatus generates the second neural network having a structure in which the existing network structure is maintained with respect to the calculation path of the existing feature amount present in the first neural network and a calculation path of the new feature amount is added. For example, the machine learning apparatus adds the new feature amount to each layer after a specific layer selected from a plurality of intermediate layers constituting the first neural network. The new feature amount added to each layer is connected to both of the existing feature amount of the immediately previous layer and the new feature amount. Meanwhile, new connection is not added between layers for the channel of the existing feature amount of each layer. That is, a connection path between layers in the second neural network is formed such that the feature map calculated using the channel of the new feature amount is not used in calculation of the feature map of the existing feature amount in the subsequent layer and is used in only calculation of the feature map of the new feature amount.

Processing of step S4 and step S5 may be combined as a single step of generating the second neural network containing the network structure of the first neural network.

In step S6, the machine learning apparatus performs learning of the second neural network using the learning data in which the image for input is associated with the label image representing the region of the pancreas in the image. At this point, a parameter of an existing feature amount group originally present in the first neural network contained in the second neural network is not changed.

That is, in a second learning step of step S6, processing of optimizing the parameter of a new feature amount group in the second neural network is performed in accordance with the algorithm of the error backpropagation method by applying a method of supervised learning using a second learning data set. The second learning data set is a collection of learning data in which the image for input is associated with a label image to which an answer label of class of the pancreas corresponding to the image is assigned. The machine learning apparatus repeats processing of updating the parameter in units of minibatches.

The machine learning apparatus repeats the learning processing until a learning finish condition is satisfied. The learning finish condition may be set based on a value of an error between an output of a prediction result and a supervisory signal or may be set based on the number of updates of the parameter. As a method based on the value of the error, for example, the learning finish condition may be such that the error falls within a prescribed range. As a method based on the number of updates, for example, the learning finish condition may be such that the number of updates reaches a prescribed number.

The learning finish condition of the re-learning performed in the second learning step may be the same condition or a different condition from the learning finish condition of the first learning step.

In step S7, the machine learning apparatus finishes second learning processing and completes the learned second neural network. That is, the machine learning apparatus determines the learning finish condition and, in a case where the learning finish condition is satisfied, finishes the second learning processing and decides the parameter of the second neural network.

Accordingly, the learned second neural network that has learned the function of segmenting four organs including the initial organ set plus the pancreas can be obtained. The learned second neural network can be used as a discriminator that segments four organs.

<Summary of Discriminator Performing Segmentation of Initial Organ Set>

Figure 4:
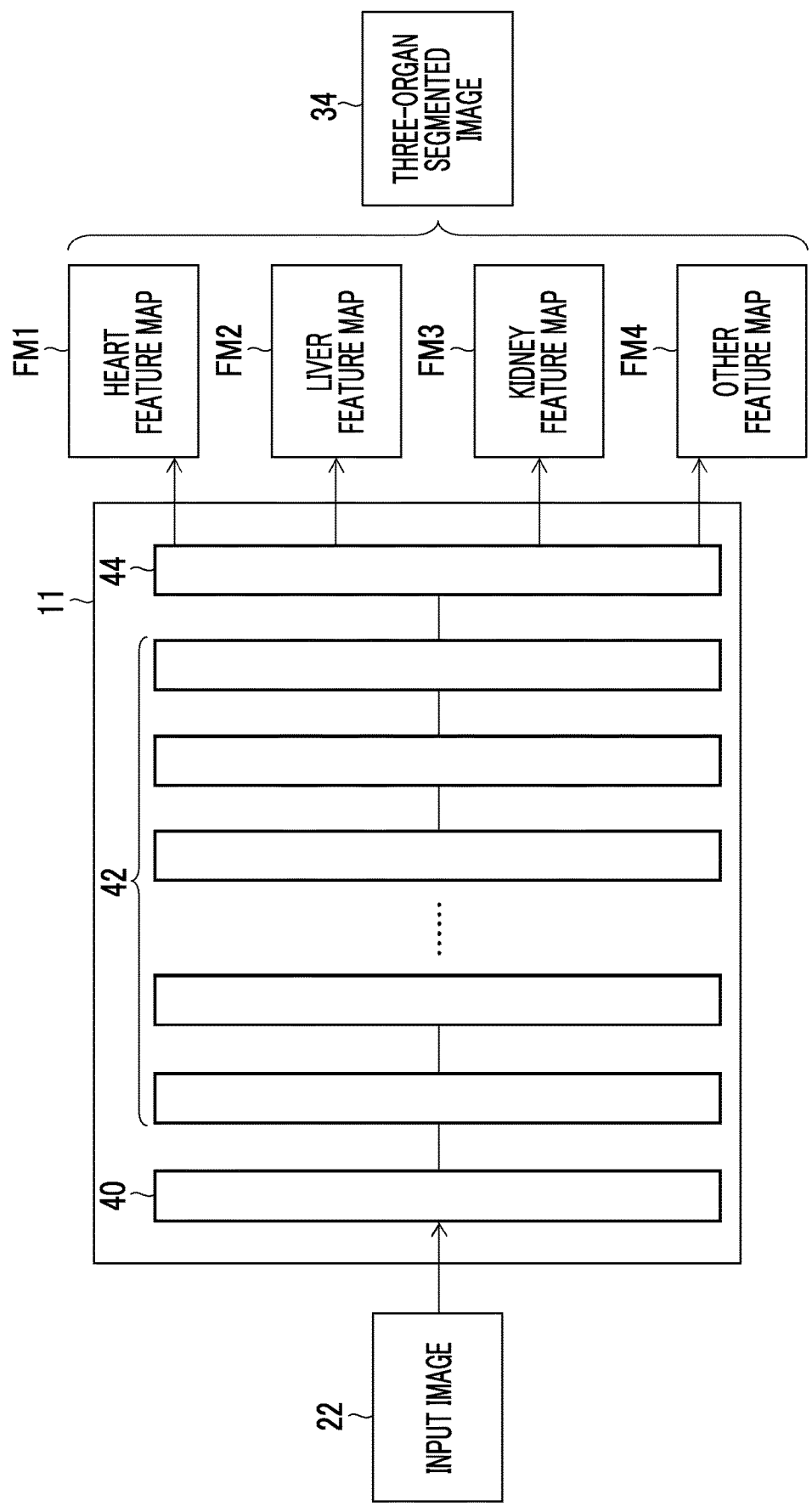
FIG. 4 is a conceptual diagram of a first neural network that has learned a task of discriminating three organs.

FIG. 4 is a conceptual diagram of the first neural network that has learned a task of discriminating three organs.

A first neural network 11 is a hierarchical neural network including an input layer 40, a plurality of intermediate layers 42, and an output layer 44. Each layer includes a plurality of "nodes". In FIG. 4, illustration of the nodes is omitted. A node belonging to a certain layer is connected to a node belonging to a layer on an output side from the certain layer. A connection weight is assigned to each inter-node connection between the nodes. Each connection weight is decided by the learning processing described using step S1 and step S2 in FIG. 3.

In the direction of flow of data from input toward output of the neural network, an input side is expressed as "front", and the output side is expressed as "rear".

The first neural network 11 includes a combination of the convolutional layer performing convolutional processing and the pooling layer performing downsampling processing in a part of the plurality of intermediate layers 42. While the layer structure of the first neural network 11 is illustrated in a simplified manner in FIG. 4, the number of layers of the intermediate layers 42 constituting the first neural network 11, the processing content of each layer, and the arrangement order of each layer are not particularly limited, and a layer structure consisting of various combinations may be employed.

The convolutional layer acquires a feature map by performing convolution calculation of applying a filter to a node present in a local region in the front layer. The convolutional layer performs feature extraction of extracting a featured intensity structure represented by the filter from the image.

The pooling layer performs pooling processing of aggregating local regions of the feature map output from the convolutional layer into a representative value. The pooling layer generates a new feature map of which the resolution is decreased by reducing the feature map output from the convolutional layer. The pooling layer provides robustness (decreases sensitivity to a positional change) such that a target feature amount extracted by the convolutional layer is not affected by a positional change.

The first neural network 11 may include one or more of at least one type of layer of a normalization layer or the unpooling layer besides the convolutional layer and the pooling layer. In addition, each layer of the intermediate layers 42 may include an activation function as necessary.

The normalization layer performs processing of normalizing the intensity of the image. For example, the normalization layer performs processing of local contrast normalization on at least one output of the output of the convolutional layer, the output of the pooling layer, or the output of the unpooling layer.

The unpooling layer performs upsampling processing in the neural network having the encoder-decoder structure. The convolutional layer used in combination with the unpooling layer may be referred to as a deconvolution layer.

The output layer 44 has the same number of channels as the number of classes for performing class classification. In the case of performing segmentation of three organs including the heart, the liver, and the kidney, the number of channels of the output layer 44 is set to four channels in order to classify data of the input image into four classification categories (classes) including "heart", "liver", "kidney", and "others" for each pixel.

In the case of performing classification of four classes, for example, a first channel is a channel for outputting a heart feature map FM1 representing the likelihood of the region of the heart. A second channel is a channel for outputting a liver feature map FM2 representing the likelihood of the region of the liver. A third channel is a channel for outputting a kidney feature map FM3 representing the likelihood of the region of the kidney. A fourth channel is a channel for outputting an other feature map FM4 representing the likelihood of other regions.

A value indicating the certainty (likelihood) of belonging to a class is calculated for the feature map (FM1 to FM4) of each channel. The value indicating the likelihood may be a normalized value or a non-normalized value.

A three-organ segmented image 34 can be obtained by performing, for example, "1×1 convolution" on the feature maps (FM1 to FM4) of all channels which are obtained from the output layer 44 by inputting an input image 22 into the first neural network 11. The 1×1 convolution is processing of combining a feature map of each channel of a plurality of feature amounts using the "1×1" filter.

<Summary of Processing in First Neural Network>

Figure 5:
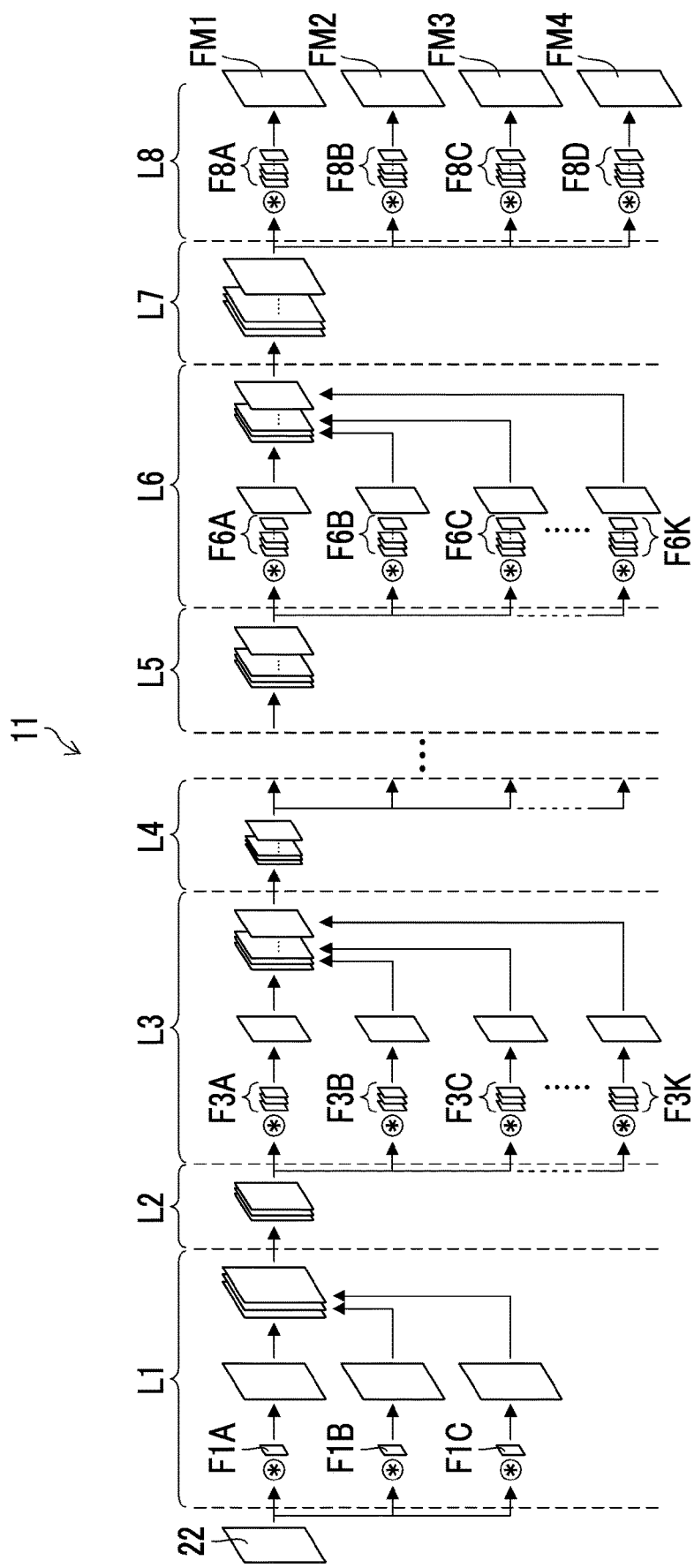
FIG. 5 is a conceptual diagram schematically illustrating a summary of processing of each layer in the first neural network.

FIG. 5 is a conceptual diagram schematically illustrating a summary of processing of each layer in the first neural network 11. In FIG. 5, a hierarchical structure including the layers L1 to L8 is illustrated by simplifying the layer structure. The layer L1 which is the first layer from the left illustrates a first convolutional layer. In the first convolutional layer, feature maps of the same number of channels as the number of types of filters are output using a plurality of types of filters. In FIG. 5, an example of outputting feature maps of three channels using three types of filters F1A, F1B, and F1C is illustrated. The feature map of each channel is obtained by applying an activation function to the output of each of the filters F1A, F1B, and F1C.

The layer L2 which is the second layer illustrates a first pooling layer. The first pooling layer performs pooling processing on the feature maps obtained in the previous layer for each channel. In FIG. 5, illustration of a filter used in a pooling operation is omitted.

The layer L3 which is the third layer illustrates a second convolutional layer. In the same manner as the first convolutional layer, the second convolutional layer outputs feature maps of the same number of channels as the number of types of filters using a plurality of types of filters F3A, F3B, F3C, . . . , F3K.

The layer L4 which is the fourth layer illustrates a second pooling layer. The second pooling layer performs the pooling processing on the feature maps obtained in the previous layer for each channel.

While illustration is not provided in FIG. 5, one or more convolutional layers, not illustrated, may be included between the layer L4 and the layer L5.

The layer L5 which is the fifth layer illustrates a first unpooling layer. The first unpooling layer performs unpooling processing on the feature maps obtained in the previous layer for each channel. The unpooling processing is referred to as up-convolution. In FIG. 5, illustration of a filter used in an unpooling operation is omitted.

The layer L6 which is the sixth layer illustrates a third convolutional layer. In the same manner as the other convolutional layers, the third convolutional layer outputs feature maps of the same number of channels as the number of types of filters using a plurality of types of filters F6A, F6B, F6C, . . . , F6K.

The layer L7 which is the seventh layer illustrates a second unpooling layer. The second unpooling layer performs the unpooling processing on the feature maps obtained in the previous layer for each channel.

The layer L8 which is the eighth layer illustrates a fourth convolutional layer. In the same manner as the other convolutional layers, the fourth convolutional layer outputs feature maps of the same number of channels as the number of types of filters using a plurality of types of filters F8A, F8B, F8C, and F8D. Here, output of the feature maps of four channels is assumed. Thus, four types of filters F8A, F8B, F8C, and F8D are used.

<Summary of Discriminator to Which Segmentation Function for Pancreas is Added>

Figure 6:
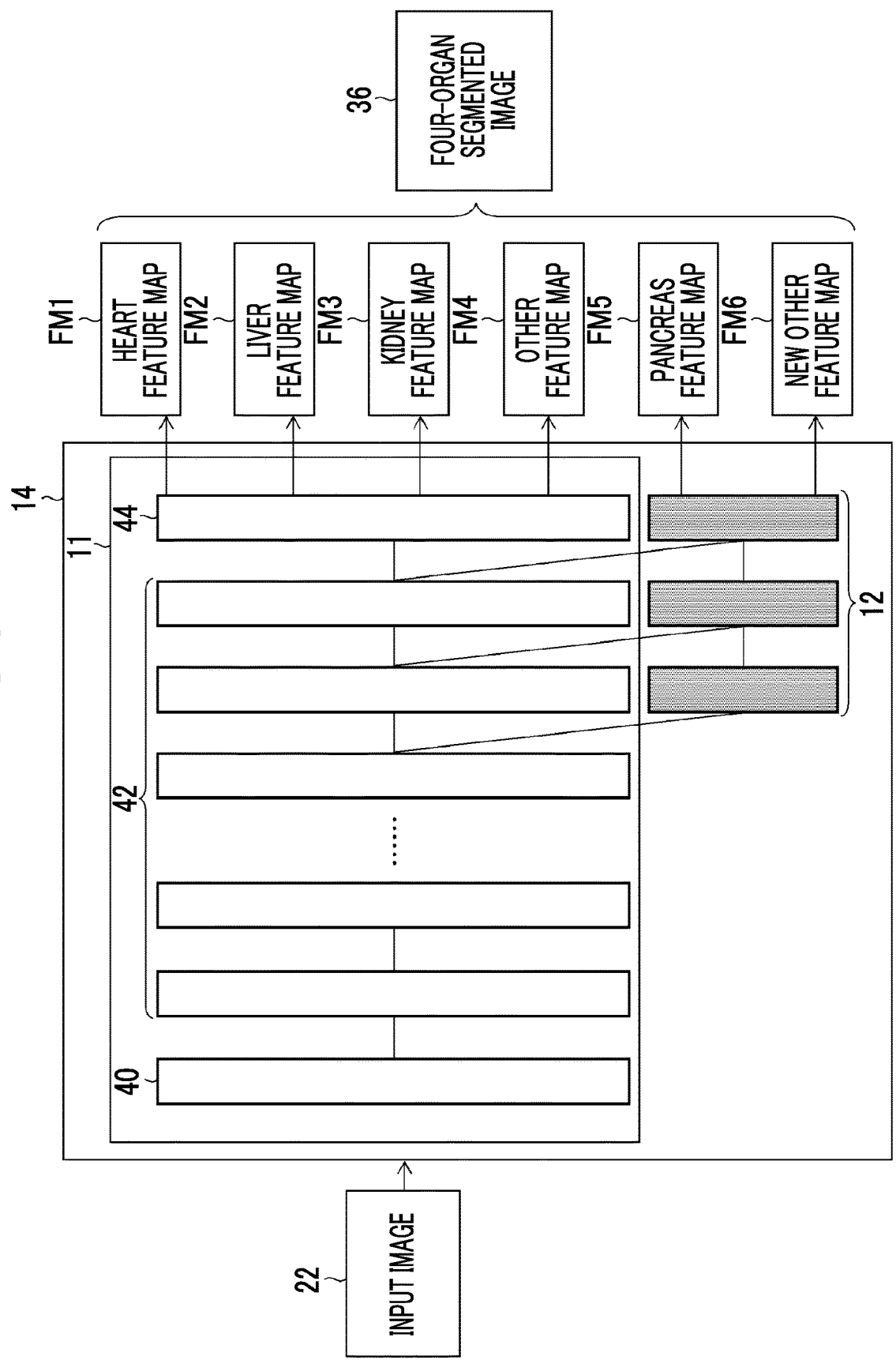
FIG. 6 is a conceptual diagram of a second neural network that has learned a task of discriminating other organs using the first neural network.

FIG. 6 is a conceptual diagram of the second neural network that has learned a task of discriminating other organs (for example, the pancreas) using the first neural network illustrated in FIG. 4.

In a second neural network 14, the network structure of the first neural network 11 is included, and a sub-network 12 for calculating the new feature amount is further added to a part of the intermediate layers 42. The sub-network 12 includes a connection relationship between a node corresponding to a feature amount calculated using a new filter for extracting a new feature and a node between layers.

The feature map of the channel of the added new feature amount is not input into the calculation path of the existing feature amount present in the first neural network 11.

In the output layer 44 of the second neural network 14, two channels corresponding to two classes including the pancreas and other than the pancreas are added in addition to the existing four channels present in the first neural network 11. The class "other than the pancreas" is referred to as "new others".

For example, a fifth channel is a channel for outputting a pancreas feature map FM5 representing the likelihood of the region of the pancreas. A sixth channel is a channel for outputting a new other feature map FM6 representing the likelihood of a region other than the pancreas.

The value indicating the certainty (likelihood) of belonging to a class is calculated for each pixel for the feature map (FM1 to FM6) of each channel. The value indicating the likelihood may be a normalized value or a non-normalized value.

A four-organ segmented image 36 can be obtained by performing, for example, "1×1 convolution" on the feature maps (FM1 to FM6) of all channels which are obtained from the output layer by inputting an input image 22 into the second neural network 14.

<Summary of Processing in Second Neural Network>

Figure 7:
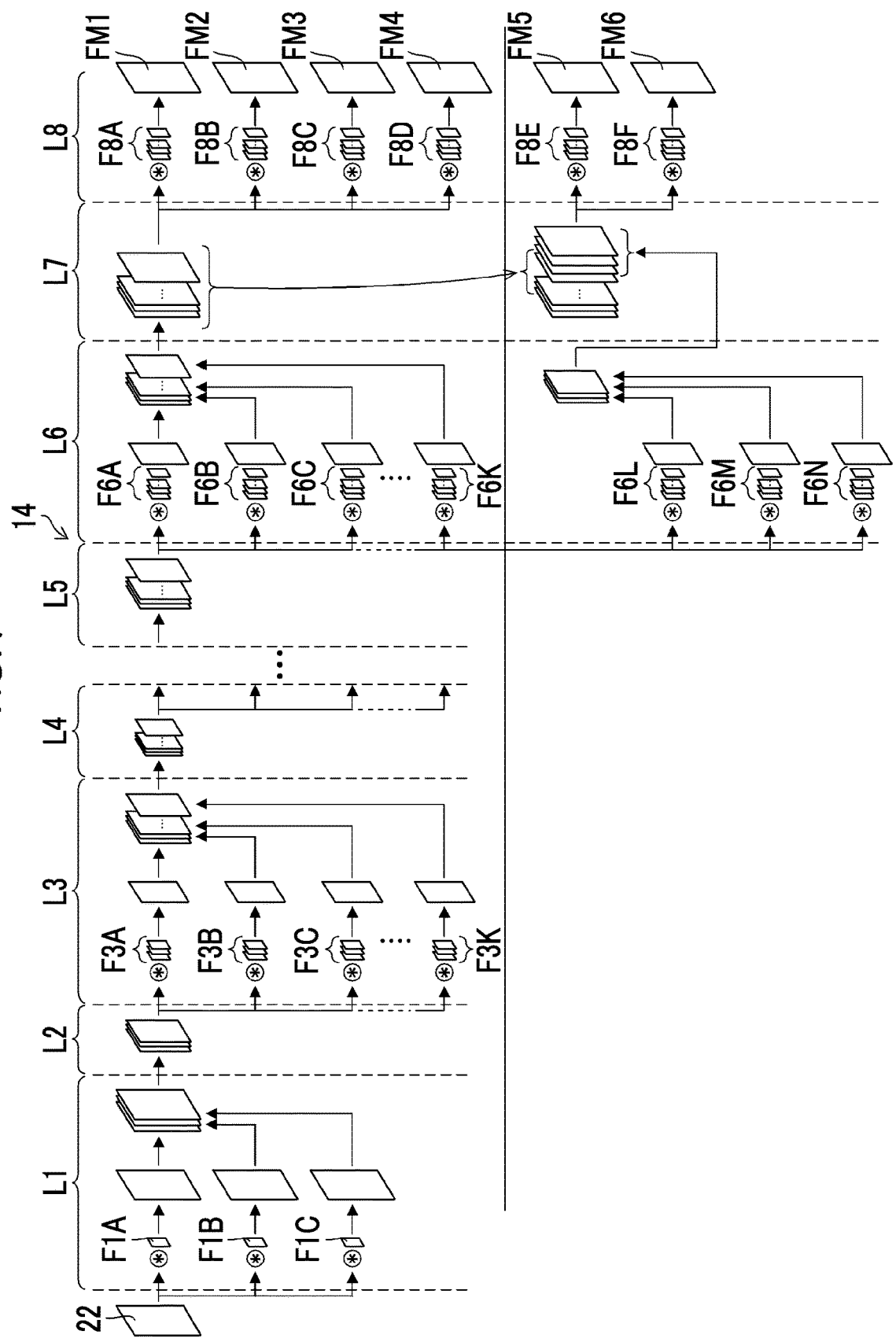
FIG. 7 is a conceptual diagram schematically illustrating a summary of processing of each layer in the second neural network.

FIG. 7 is a conceptual diagram schematically illustrating a summary of processing of each layer in the second neural network 14. Differences from the first neural network 11 illustrated in FIG. 6 will be described. The second neural network 14 illustrated in FIG. 7 is configured by adding the new feature amount to each layer after the layer L6 in the first neural network 11 illustrated in FIG. 6.

New filters F6L, F6M, and F6N are added to the layer L6 which is the sixth layer. The layer L6 maintains an output path of the feature map of each channel by convolving the existing filters F6A, F6B, F6C, . . . , F6K and outputs a feature map of a new channel by convolving the new filters F6L, F6M, and F6N.

The layer L7 which is the seventh layer maintains an output path of the feature map of the existing channel and outputs the feature map of the new channel.

New filters F8E and F8F are added to the layer L8 which is the eighth layer. The layer L8 maintains the output path of the feature map of each channel by convolving the existing filters F8A, F8B, F8C, and F8D and outputs the feature map of the new channel by convolving the new filters F8E, and F8F. Here, it is assumed that output of the feature maps of two channels corresponding to two classes including the pancreas and other than the pancreas is added in addition to the output of the feature maps of four channels corresponding to the existing four classes. Thus, two types of filters F8E and F8F are used. The number of channels of each of the filters F8E and F8F is the same as the number of all channels of the feature maps output from the layer L7.

The size of the filter and the number of filters are appropriately designed in accordance with the task of class classification set as the aim.

<Example of System Configuration>

Figure 8:
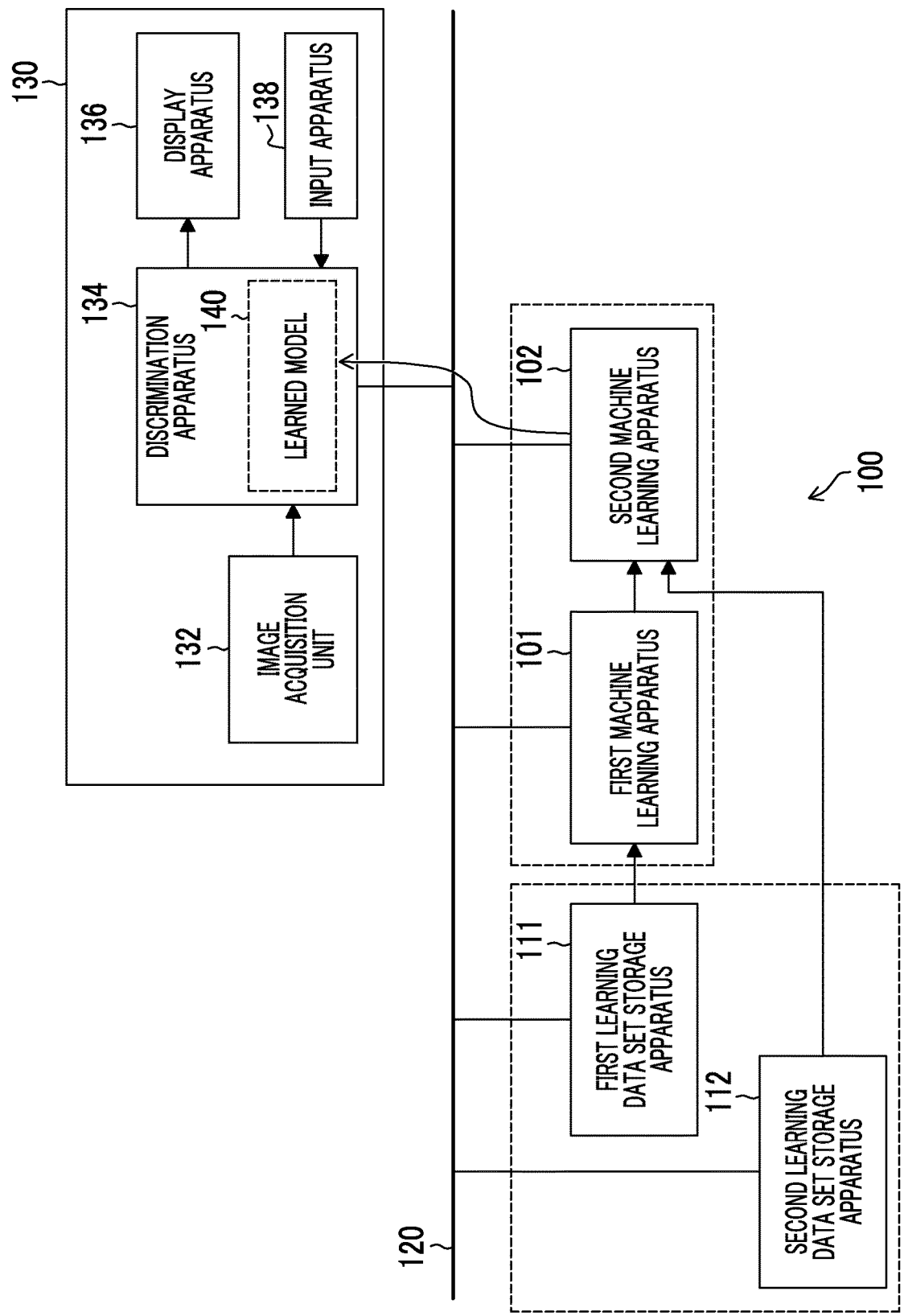
FIG. 8 is a block diagram illustrating a configuration example of a machine learning system performing learning of a neural network and an image processing system using a learned model.

FIG. 8 is a block diagram illustrating a configuration example of a machine learning system performing learning of the neural network and an image processing system using the learned model.

A machine learning system 100 illustrated in FIG. 8 includes a first machine learning apparatus 101, a second machine learning apparatus 102, a first learning data set storage apparatus 111, and a second learning data set storage apparatus 112. The first machine learning apparatus 101 and the second machine learning apparatus 102 are configured using one or a plurality of computers. The functions of the first machine learning apparatus 101 and the second machine learning apparatus 102 may be collectively configured as one machine learning apparatus.

The first machine learning apparatus 101 executes processing of step S1 and step S2 in FIG. 3. The first learning data set storage apparatus 111 is a data storage apparatus storing the first learning data set which is a set of learning data consisting of a pair of the image for input used for learning the task of classifying the initial organ set and the label image to which the answer label corresponding to the image is assigned.

The first machine learning apparatus 101 performs the first learning processing using the first learning data set stored in the first learning data set storage apparatus 111 and completes the first neural network 11 that has acquired the processing function of the class classification related to the initial organ set.

The second machine learning apparatus 102 executes processing of step S3 to step S7 in FIG. 3. The second learning data set storage apparatus 112 is a data storage apparatus storing the second learning data set which is a set of learning data consisting of the image for input used for learning the task of classifying the organ (here, the pancreas is illustrated) belonging to the new class and the label image to which the answer label corresponding to the image is assigned.

The second machine learning apparatus 102 performs the second learning processing using the second learning data set stored in the second learning data set storage apparatus 112 and completes the second neural network 14 that has acquired the processing function of the class classification related to the new organ (for example, the pancreas).

The first learning data set storage apparatus 111 and the second learning data set storage apparatus 112 are configured to include, for example, a hard disk apparatus, an optical disk, a magneto-optical disk, or a semiconductor memory, or a storage apparatus configured by means of an appropriate combination thereof.

The first machine learning apparatus 101, the second machine learning apparatus 102, the first learning data set storage apparatus 111, and the second learning data set storage apparatus 112 are connected to each other through an electric communication line 120. The term "connection" is not limited to wired connection and includes the concept of wireless connection.

The electric communication line 120 may be a local area network or a wide area network. The electric communication line 120 is configured with an appropriate wired and wireless combination.

The first learning data set storage apparatus 111 may be a storage apparatus of the computer constituting the first machine learning apparatus 101. The second learning data set storage apparatus 112 may be a storage apparatus of the computer constituting the second machine learning apparatus 102.

The functions of the first learning data set storage apparatus 111 and the second learning data set storage apparatus 112 may be collectively configured as one learning data set storage apparatus. In addition, a part or all of the functions of the first machine learning apparatus 101, the second machine learning apparatus 102, the first learning data set storage apparatus 111, and the second learning data set storage apparatus 112 can be implemented by cloud computing.

An image processing system 130 using a learned model 140 learned by the second machine learning apparatus 102 is a data processing system handling medical images and comprises an image acquisition unit 132 and a discrimination apparatus 134. In addition, the image processing system 130 comprises a display apparatus 136 and an input apparatus 138 as a user interface.

The image processing system 130 may be configured as one data processing apparatus or may be configured by combining a plurality of apparatuses. For example, the image processing system 130 can be implemented using one or a plurality of computers. The image processing system 130 can be used as a diagnosis assistance apparatus that assists medical examination, treatment, diagnosis, or the like performed by a doctor or the like. The term "diagnosis assistance" includes the concept of medical examination assistance and/or treatment assistance.

The image acquisition unit 132 is an interface for acquiring a processing target image. For example, the image acquisition unit 132 may be a connector terminal connected to an image processor of a CT apparatus, not illustrated, or may be a signal input terminal of a signal processing circuit mounted in the discrimination apparatus 134. Alternatively, the image acquisition unit 132 may be a communication network terminal, a media interface terminal for external storage media, or a connection terminal for an external apparatus, or an appropriate combination thereof.

The image acquisition unit 132 may include an image generation apparatus that generates the processing target image. The image generation apparatus may be one or a combination of various medical apparatuses such as a CT apparatus, an X-ray diagnosis apparatus, an ultrasound diagnostic apparatus, an MRI apparatus, an electronic endoscope apparatus, a nuclear medicine diagnosis apparatus, or a fundus camera.

The discrimination apparatus 134 includes the learned model 140 that acquires processing performance for multi-class classification by machine learning. In the initial stage, the learned model 140 may be a model that acquires recognition performance related to the initial organ set learned using the first machine learning apparatus 101. Then, as necessary, the second machine learning apparatus 102 performs the re-learning of the new task using the existing learned model and replaces the model with the new learned model 140.

Such a configuration of replacing an old module with a new module is not for limitation purposes. The new learned model 140 (new module) may be originally mounted in the discrimination apparatus 134.

The discrimination apparatus 134 receives an input of the image acquired through the image acquisition unit 132 and outputs a discrimination result for the image. In the case of the present example, the prediction result of segmentation of multiple organs is output. The discrimination result of the discrimination apparatus 134 may be displayed on the display apparatus 136 as the segmented image. In addition, the volume rendering image may be displayed on the display apparatus 136 instead of or in combination with the segmented image. The discrimination apparatus 134 may be incorporated inside, for example, a processor apparatus connected to the CT apparatus.

The display apparatus 136 may be, for example, a liquid crystal display, an organic electro-luminescence (EL) (OEL) display, or a projector, or an appropriate combination thereof. Besides the discrimination result, the display apparatus 136 may display the processing target image and various information such as various setting information necessary for processing.

The input apparatus 138 may be, for example, an operation button or a keyboard, a mouse, a touch panel, or a voice input apparatus, or an appropriate combination thereof. The user can input various instructions by operating the input apparatus 138.

The image processing system 130, for example, may be installed in an operating room or an examination room in a hospital or a conference room or may be installed in a medical institution that is a facility outside the hospital, or a research institution. The discrimination apparatus 134 may be a workstation assisting medical examination, treatment, diagnosis, and the like or may be a work assistance apparatus assisting medical works. The work assistance apparatus may have a function of performing accumulation of clinical information, assistance of creating a diagnosis document, assistance of creating a report, and the like.

<Configuration Example of First Machine Learning Apparatus>

Figure 9:
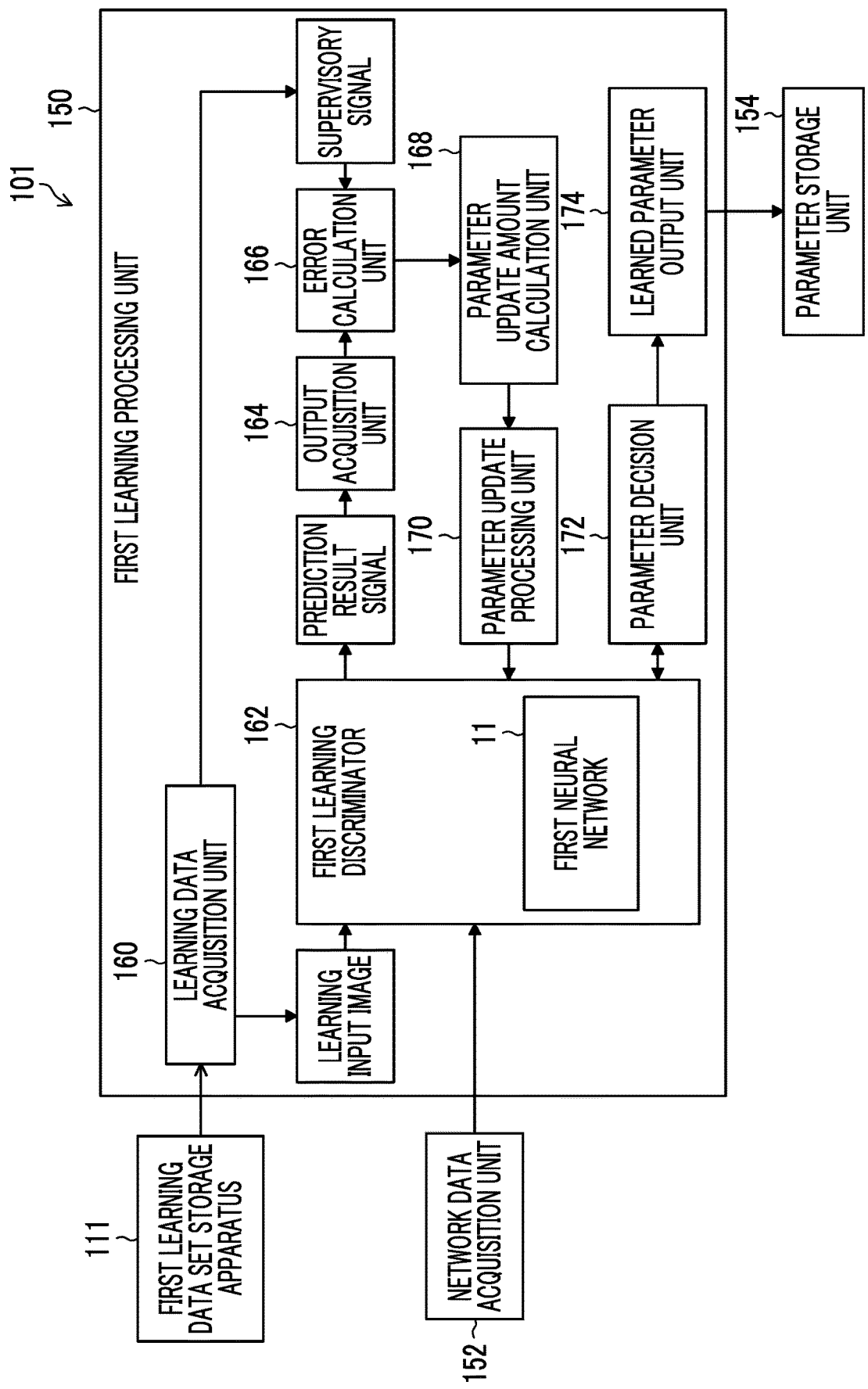
FIG. 9 is a block diagram illustrating functions of a first machine learning apparatus.

FIG. 9 is a block diagram illustrating the functions of the first machine learning apparatus 101. The first machine learning apparatus 101 includes a first learning processing unit 150, a network data acquisition unit 152, and a parameter storage unit 154. The first learning processing unit 150 includes a learning data acquisition unit 160, a first learning discriminator 162, an output acquisition unit 164, an error calculation unit 166, a parameter update amount calculation unit 168, a parameter update processing unit 170, a parameter decision unit 172, and a learned parameter output unit 174. A display apparatus and an input apparatus, not illustrated, may be connected to the first machine learning apparatus 101.

The network data acquisition unit 152 is a data input interface for acquiring network data that prescribes the network structure in the first neural network 11 used in the first learning discriminator 162. For example, the network data includes information indicating the layer structure of the network and the size of the filter and the number of filters used in each layer. In the stage before completion of learning, the first neural network 11 may be in a state where parameters such as a coefficient of the filter convolved in each layer and a bias of the node are not confirmed. The coefficient of the filter corresponds to the "connection weight" between nodes between layers.

The network data acquisition unit 152 may be a communication interface for connection to the electric communication line 120 or a media interface for reading the program module. Alternatively, the network data acquisition unit 152 may be an input interface for acquiring information from the input apparatus, not illustrated.

The learning data acquisition unit 160 is an interface for acquiring the learning data from the first learning data set storage apparatus 111. For example, the learning data acquisition unit 160 may be a communication interface for connection to the electric communication line 120. A learning input image of the learning data acquired through the learning data acquisition unit 160 is input into the first learning discriminator 162.

The first learning discriminator 162 is a discriminator comprising the same configuration as the neural network incorporated in the discrimination apparatus 134. The first learning discriminator 162 performs discrimination processing using the learning input image as an input signal and outputs a prediction result signal indicating a processing result.

The output acquisition unit 164 acquires the prediction result signal output from the first neural network 11 of the first learning discriminator 162. The prediction result signal is input into the error calculation unit 166 through the output acquisition unit 164. The output acquisition unit 164 may be an input unit of the error calculation unit 166.

The error calculation unit 166 calculates an error between the supervisory signal of the label image corresponding to the learning input image input in the first learning discriminator 162 and the prediction result signal actually obtained from the first learning discriminator 162. The error calculated by the error calculation unit 166 is transmitted to the parameter update amount calculation unit 168.

The parameter update amount calculation unit 168 calculates an update amount of the parameter of the first neural network 11 based on the error calculated by the error calculation unit 166. For example, the parameter update amount calculation unit 168 calculates the update amount of the parameter in units of minibatches.

The parameter update processing unit 170 performs processing of updating the parameter of the first neural network 11 in accordance with the update amount calculated by the parameter update amount calculation unit 168.

The parameter decision unit 172 finishes learning in accordance with the predetermined learning finish condition and decides the parameter of the first neural network 11 in the first learning discriminator 162. The decided learned parameter is stored in the parameter storage unit 154 through the learned parameter output unit 174.

The learned parameter output unit 174 is an output interface for outputting the learned parameter decided by the parameter decision unit 172 to the outside. For example, the learned parameter output unit 174 may be a communication interface or a signal output terminal.

The parameter storage unit 154 stores data and/or a program module specifying the learned model 140.

<Configuration Example of Second Machine Learning Apparatus>

Figure 10:
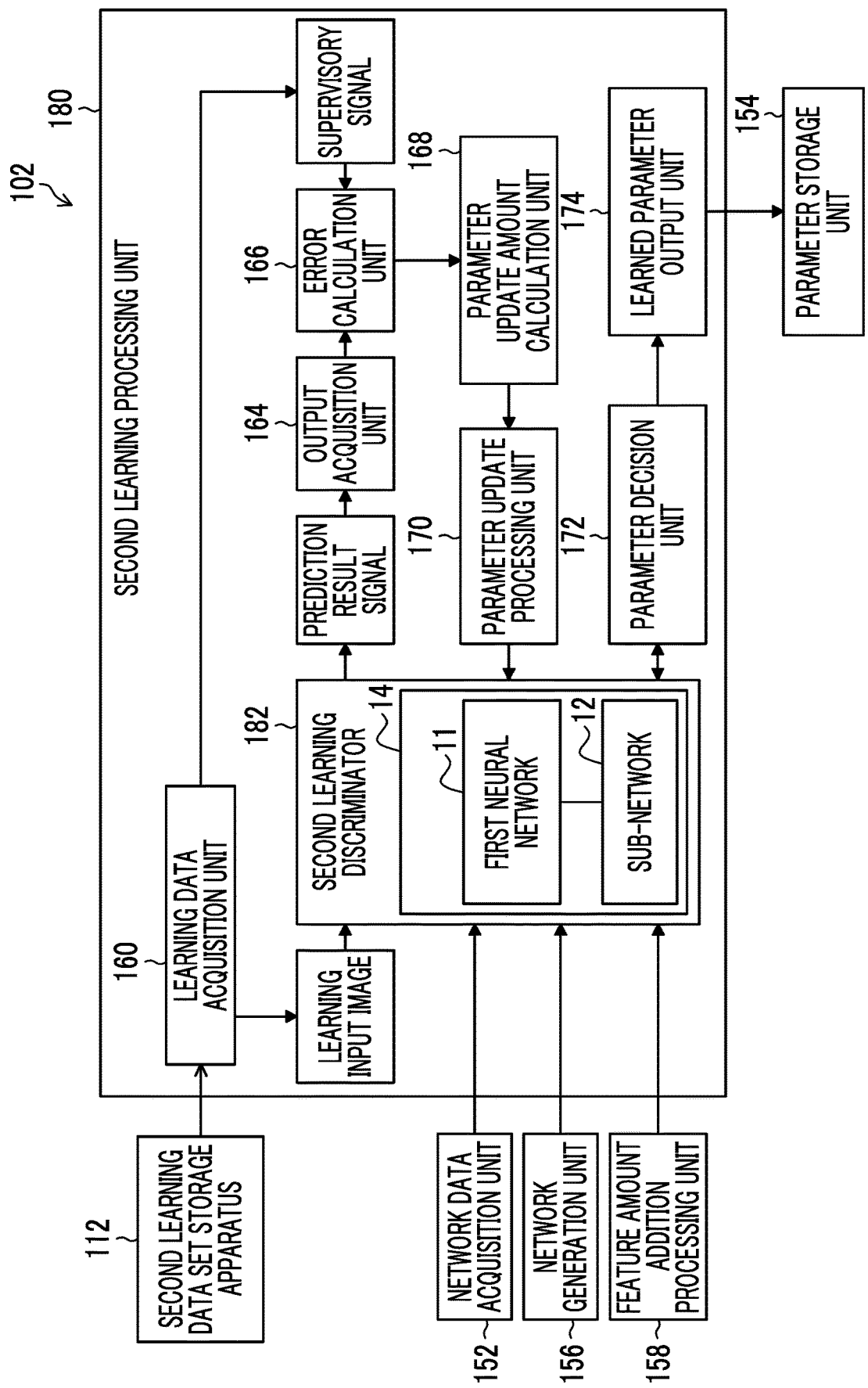
FIG. 10 is a block diagram illustrating functions of a second machine learning apparatus.

FIG. 10 is a block diagram illustrating the functions of the second machine learning apparatus 102. In FIG. 10, the same or similar elements to FIG. 9 are designated by the same reference signs, and descriptions of such elements will be omitted. Differences from FIG. 9 will be mainly described.

The second machine learning apparatus 102 includes a second learning processing unit 180, the network data acquisition unit 152, a network generation unit 156, and a feature amount addition processing unit 158. The second learning processing unit 180 has the same configuration as the first learning processing unit 150 described using FIG. 9 and includes a second learning discriminator 182 instead of the first learning discriminator 162.

The second learning processing unit 180 acquires data of the learned first neural network 11 through the network data acquisition unit 152.

The network generation unit 156 generates the second neural network 14 used in the second learning discriminator 182 in cooperation with the feature amount addition processing unit 158.

The feature amount addition processing unit 158 performs processing of adding the new feature amount to at least one intermediate layer included in the first neural network 11. The feature amount addition processing unit 158 performs processing of step S4 in FIG. 3.

The network generation unit 156 generates the second neural network 14 having a structure in which the structure of the first neural network 11 is maintained without connecting the new feature amount with respect to the calculation path of the existing feature amount present in the learned first neural network 11 and the new feature amount to be added in the subsequent layer is calculated by performing processing of convolving each of the existing feature amount and the new feature amount with respect to the calculation path of the new feature amount.

The network generation unit 156 generates the second neural network 14 by generating the sub-network 12 corresponding to the calculation path of the new feature amount added by the feature amount addition processing unit 158 and adding the sub-network 12 to the learned first neural network 11.

The learning data acquisition unit 160 is an interface for acquiring the learning data from the second learning data set storage apparatus 112. The learning input image of the learning data acquired through the learning data acquisition unit 160 is input into the second learning discriminator 182.

The second learning processing unit 180 including the second learning discriminator 182 performs processing of step S6 and step S7 in FIG. 3. The operation of the second learning processing unit 180 is the same as the operation of the first learning processing unit 150 described using FIG. 9. Thus, description of the operation will be omitted.

The learned parameter decided by the second learning processing unit 180 can be provided to the discrimination apparatus 134 (refer to FIG. 7) through the learned parameter output unit 174. Accordingly, the learned model 140 in the discrimination apparatus 134 can be updated to an up-to-date model.

The second machine learning apparatus 102 incorporates the function of the first machine learning apparatus 101. Thus, the second machine learning apparatus 102 can be used as the first machine learning apparatus 101.

<Generalization of Task of Class Classification>

In the first embodiment, the segmentation function for three organs including the heart, the liver, and the kidney is described as a specific example of a class included in first class classification, and an example of adding the segmentation function for one organ (for example, the pancreas) is described as a specific example of a class included in second class classification to be newly added. However, the number of classes included in the first class classification and the number of classes included in the second class classification are not limited to the above example and can be set to any number of classes.

The object on which class classification is performed is not limited to the "organs", and the neural network can learn to classify various objects depending on the content of the image.

Figure 11:
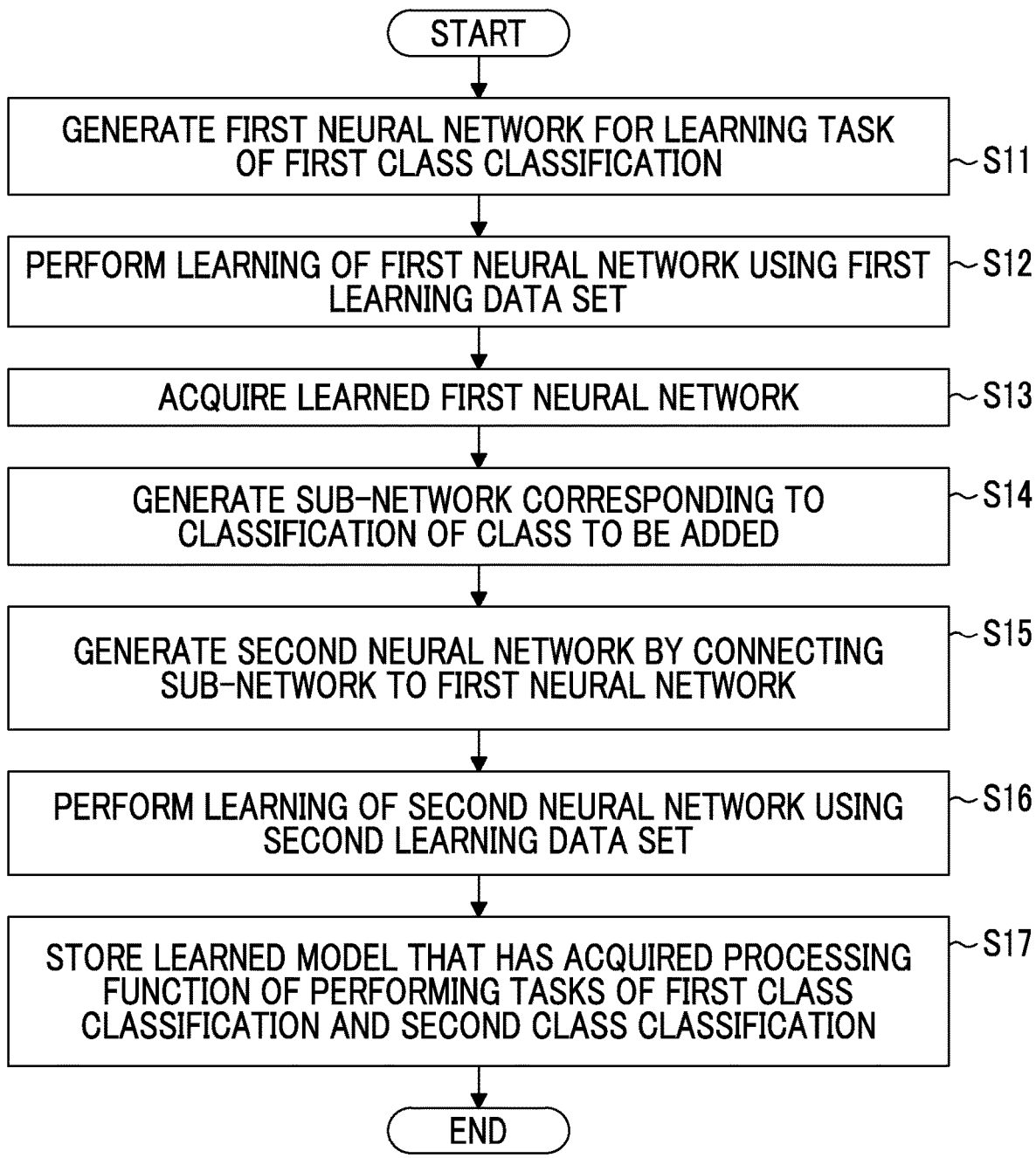
FIG. 11 is a flowchart in which the machine learning method according to the first embodiment is rewritten in more general content.

FIG. 11 is a flowchart in which the machine learning method according to the first embodiment is rewritten in more general content.

In step S11, the machine learning apparatus generates the first neural network that learns a task of the first class classification.

In step S12, the machine learning apparatus performs learning of the first neural network using the first learning data set. The learned first neural network is completed by the learning processing in step S12.

Processing of step S11 to step S12 may be performed by the first machine learning apparatus 101 (refer to FIG. 8 and FIG. 9).

In step S13, the machine learning apparatus acquires the learned first neural network.

In step S14, the machine learning apparatus generates the sub-network for calculating the new feature amount corresponding to classification of the class to be added.

In step S15, the machine learning apparatus generates the second neural network by connecting the sub-network to the learned (existing) first neural network.

In step S16, the machine learning apparatus performs learning of the second neural network using the second learning data set. At this point, a parameter related to the existing feature amount in the learned first neural network is not changed.

The second neural network that acquires a processing function of performing a task of the second class classification is obtained through the second learning processing in step S16.

In step S17, the machine learning apparatus stores the learned model that acquires the processing function of performing the tasks of the first class classification and the second class classification in a storage unit. The storage unit may be an internal memory of the machine learning apparatus or an external storage apparatus connected to the machine learning apparatus.

Processing of step S13 to step S17 may be performed by the second machine learning apparatus 102 (refer to FIG. 8 and FIG. 10).

<Second Embodiment>

While an example including processing of performing learning of the first neural network 11 is described in the first embodiment, the learned first neural network 11 may be prepared in advance. For example, processing of step S1 and step S2 illustrated in FIG. 3 may be omitted. In addition, processing of step S11 and step S12 illustrated in FIG. 11 may be omitted.

Figure 12:
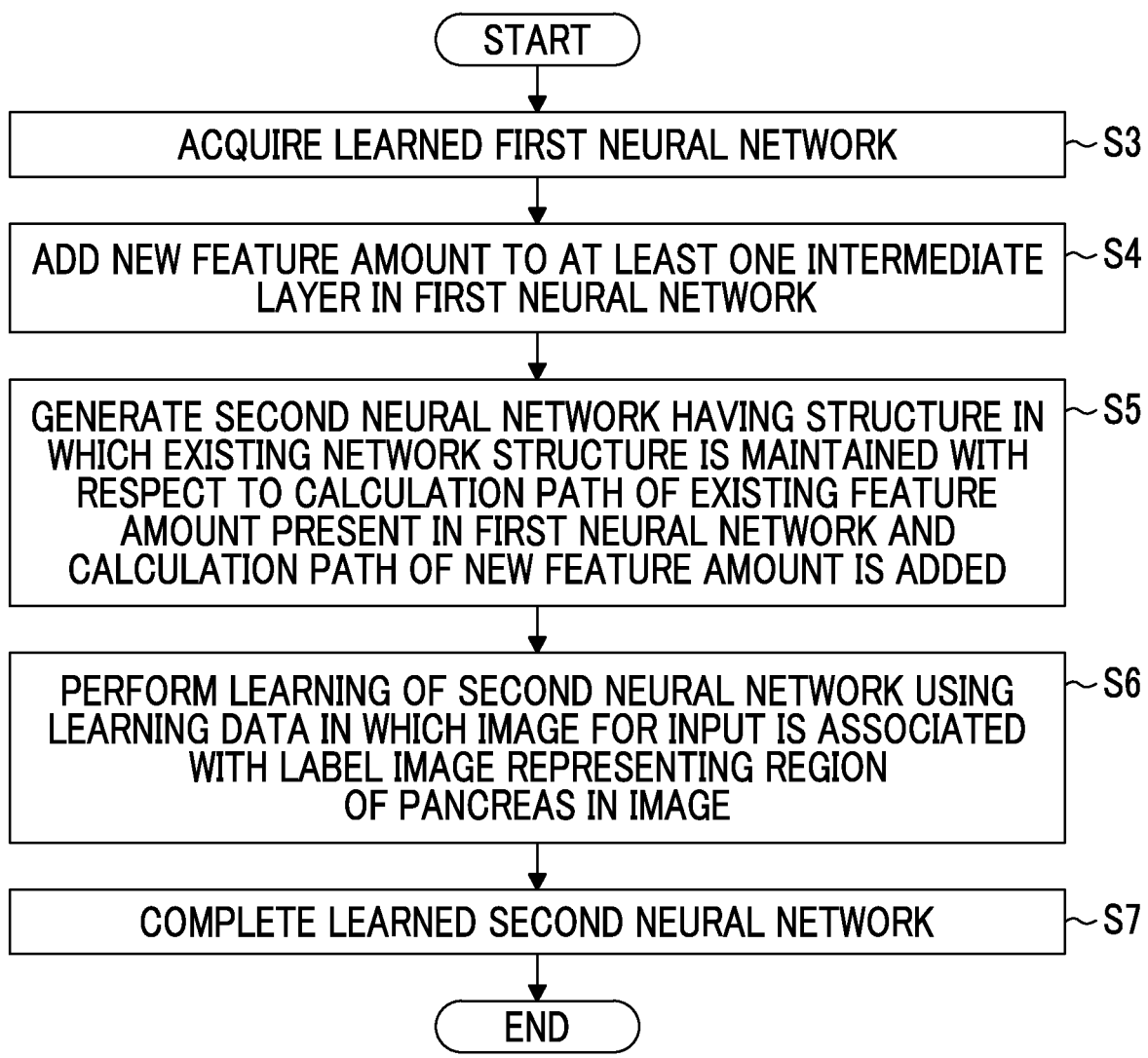
FIG. 12 is a flowchart illustrating a procedure of a machine learning method according to a second embodiment.

FIG. 12 is a flowchart illustrating a procedure of a machine learning method according to a second embodiment. In FIG. 12, the same processing as the flowchart illustrated in FIG. 3 is designated by the same step numbers, and description of such processing will be omitted.

In the machine learning method illustrated in FIG. 12, generation and learning of the second neural network 14 are performed using the learned first neural network 11 based on assumption that the learned first neural network 11 already exists.

The second machine learning apparatus 102 described using FIG. 10 may perform the machine learning method according to the second embodiment.

<Advantage of Each Embodiment>

According to the machine learning method and the machine learning apparatus according to each embodiment, for example, the following advantages are achieved.

(1) A new neural network (second neural network) to which a processing function of another task is added without changing the output performance of the learned first neural network can be provided.

(2) For example, after the learned first neural network is released on the market as a first discrimination module, a new module (second discrimination module) to which the processing function of another task is added without changing the output performance of the released module can be provided.

(3) Since a part of the feature amounts is shared between the released old module and the new module to which the function is added, the calculation amount is controlled, and the execution speed of calculation can be maintained at a high speed.

<Modification Example 1>

While the task of segmentation of dividing each pixel (each voxel) into a class is described as an example of the multiclass classification in each embodiment, the application scope of the present invention is not limited to the task of segmentation and can be applied to a task of performing class classification in units of images. Each of the first neural network and the second neural network is not limited to a fully convolutional network and may have a network structure comprising a fully connected layer in at least one layer other than the output layer.

<Modification Example 2>

In the case of embodying the present invention, the present invention is not limited to a task of classifying a plurality of organs from the CT image and can be applied to various tasks. For example, the present invention can be used even in the case of performing a task of discriminating a lesion region from an endoscope image. In addition, the present invention can be used in the case of performing segmentation of classifying an image of a scene into a region of one or a plurality of target objects.

<Modification Example 3>

The present invention can be applied to the field of video monitoring. For example, the present invention can be used for extracting a person, a suspicious person, or the like from a motion picture imaged using a monitoring camera or the like. In addition, the present invention can be used for extracting a target object such as a road traffic sign, a person, and a vehicle from a motion picture imaged using a vehicle-mounted camera.

<Modification Example 4>

The present invention is not limited to the field of image recognition and can also be applied to a system performing processing such as voice recognition or language recognition.

<Hardware Configuration of Each Processing Unit>

For example, hardware structures of various control units and processing units executing processing such as the first learning processing unit 150, the network data acquisition unit 152, the network generation unit 156, the feature amount addition processing unit 158, the learning data acquisition unit 160, the first learning discriminator 162, the output acquisition unit 164, the error calculation unit 166, the parameter update amount calculation unit 168, the parameter update processing unit 170, the parameter decision unit 172, the first neural network 11, the sub-network 12, and the second neural network 14 described using FIG. 9 and FIG. 10 include the following various processors.

The various processors include a CPU that is a general-purpose processor functioning as various processing units by executing a program, a GPU that is a processor specialized in image processing, a programmable logic device (PLD) such as a field programmable gate array (FPGA) that is a processor having a circuit configuration changeable after manufacturing, a dedicated electric circuit such as an application specific integrated circuit (ASIC) that is a processor having a circuit configuration dedicatedly designed to execute a specific type of processing, and the like.

One processing unit may be configured with one of the various processors or may be configured with two or more processors of the same type or different types. For example, one processing unit may be configured with a plurality of FPGAs, a combination of a CPU and an FPGA, or a combination of a CPU and a GPU. In addition, a plurality of processing units may be configured with one processor. As an example of configuring the plurality of processing units with one processor, first, as represented by a computer such as a client or a server, a form of configuring one processor with a combination of one or more CPUs and software and causing the processor to function as the plurality of processing units is present. Second, as represented by a system on chip (SoC) or the like, a form of using a processor that implements the function of the entire system including the plurality of processing units using one integrated circuit (IC) chip is present. Accordingly, various processing units are configured by means of one or more of the various processors as a hardware structure.

Furthermore, the hardware structure of the various processors is more specifically an electric circuit (circuitry) in which circuit elements such as semiconductor elements are combined.

<Example of Hardware Configuration of Computer>

Figure 13:
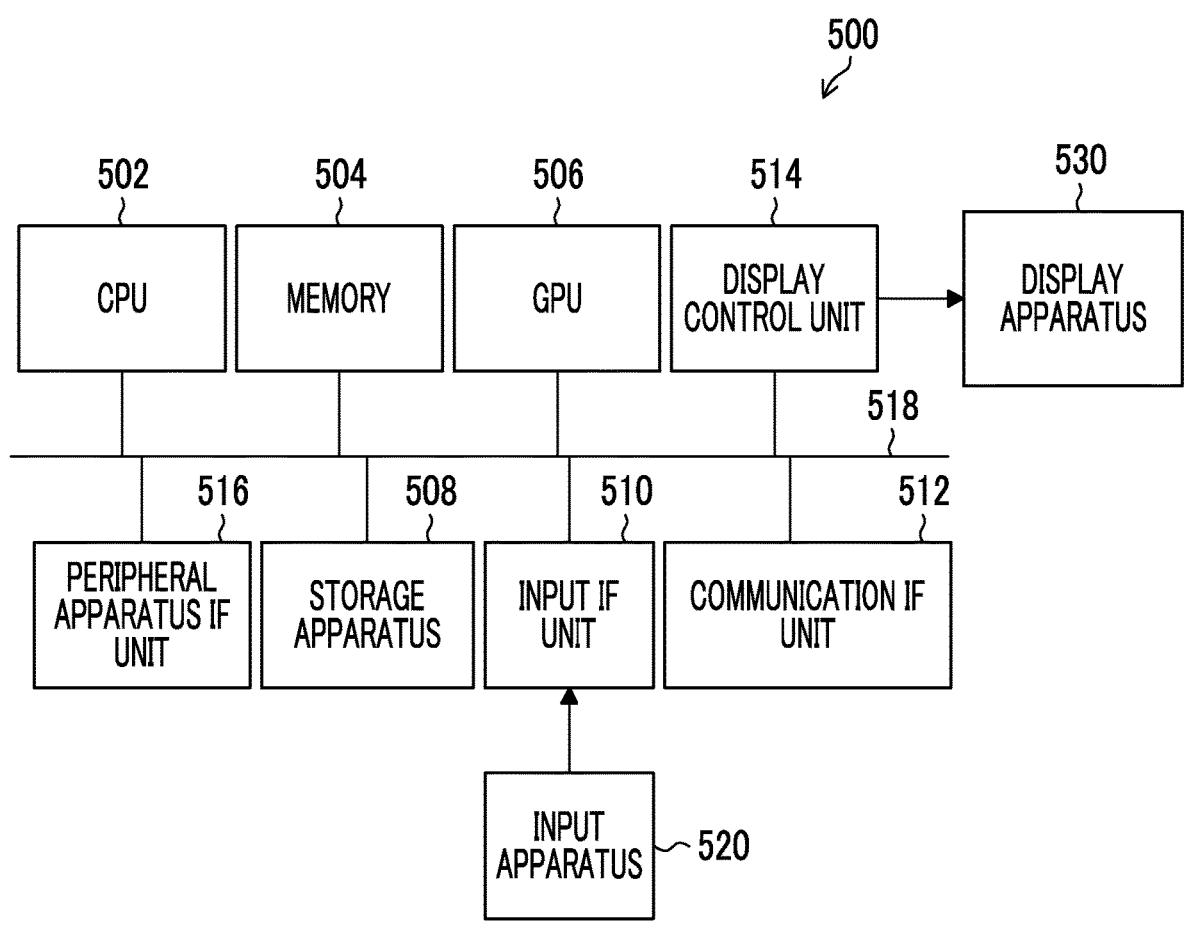
FIG. 13 is a block diagram illustrating an example of a hardware configuration of a computer.

FIG. 13 is a block diagram illustrating an example of a hardware configuration of a computer that can be used as the first machine learning apparatus 101, the second machine learning apparatus 102, or the discrimination apparatus 134, or an apparatus having a plurality of functions thereof. The computer includes computers of various forms such as a desktop type, a laptop type, or a tablet type. In addition, the computer may be a server computer or a microcomputer.

A computer 500 comprises a CPU 502, a memory 504, a GPU 506, a storage apparatus 508, an input interface unit 510, a communication interface unit 512 for network connection, a display control unit 514, a peripheral apparatus interface unit 516, and a bus 518. In FIG. 13, "IF" denotes an "interface".

The storage apparatus 508 may be configured by means of, for example, a hard disk apparatus. The storage apparatus 508 stores various programs, data, and the like necessary for image processing such as the learning processing and/or the recognition processing. By loading a program stored in the storage apparatus 508 into the memory 504 and causing the CPU 502 to execute the program, the computer functions as a unit performing various types of processing prescribed by the program. The storage apparatus 508 can be used as the first learning data set storage apparatus 111 and/or the second learning data set storage apparatus 112.

An input apparatus 520 is connected to the input interface unit 510. A display apparatus 530 is connected to the display control unit 514. The input apparatus 520 and the display apparatus 530 may function as the input apparatus 138 and the display apparatus 136 described using FIG. 8.

<Program Operating Computer>

A program that causes the computer to implement at least one processing function of the learning function based on the machine learning method described in each embodiment or the processing function of class classification using the neural network can be recorded on a computer readable medium that is a tangible non-transitory information storage medium such as an optical disk, a magnetic disk, or a semiconductor memory, and the program can be provided through the information storage medium. Alternatively, instead of the aspect of providing the program by storing the program in the tangible non-transitory information storage medium, a program signal can be provided as a download service using an electric communication line such as the Internet.

In addition, a part or all of at least one processing function of the learning function based on the machine learning method described in each embodiment or the processing function of class classification using the neural network can be provided as an application server, and a service providing the processing function through the electric communication line can be performed.

[Others]

The constituents of the embodiments of the present invention described above can be appropriately changed, added, or removed without departing from the gist of the present invention. The present invention is not limited to the embodiments described above, and various modifications can be made by those having ordinary knowledge in the equivalent or relevant field within the technical idea of the present invention.

Explanation of References
  10, 10A: neural network
  11: first neural network
  12: sub-network
  14: second neural network
  20: CT image
  22: input image
  30: segmented CT image
  32: volume rendering image
  34: three-organ segmented image
  36: four-organ segmented image
  40: input layer
  42: intermediate layer
  44: output layer
  100: machine learning system
  101: first machine learning apparatus
  102: second machine learning apparatus
  111: first learning data set storage apparatus
  112: second learning data set storage apparatus
  120: electric communication line
  130: image processing system
  132: image acquisition unit
  134: discrimination apparatus
  136: display apparatus
  138: input apparatus
  140: learned model
  150: first learning processing unit
  152: network data acquisition unit
  154: parameter storage unit
  156: network generation unit
  158: feature amount addition processing unit
  160: learning data acquisition unit
  162: first learning discriminator
  164: output acquisition unit
  166: error calculation unit
  168: parameter update amount calculation unit
  170: parameter update processing unit
  172: parameter decision unit
  174: learned parameter output unit
  180: second learning processing unit
  182: second learning discriminator
  500: computer
  504: memory
  508: storage apparatus
  510: input interface unit
  512: communication interface unit
  514: display control unit
  516: peripheral apparatus interface unit
  518: bus
  520: input apparatus
  530: display apparatus
  C1 to C15: convolutional layer
  P1 to P3: pooling layer
  U1 to U3: unpooling layer
  F1A to F1C: filter
  F3A to F3K: filter
  F6A to F6N: filter
  F8A to F8F: filter
  FM1: heart feature map
  FM2: liver feature map
  FM3: kidney feature map
  FM4: other feature map
  FM5: pancreas feature map
  FM6: new other feature map
  L1 to L8: layer
  S1 to S7: step of processing of machine learning method
  S11 to S17: step of processing of machine learning method

What is claimed is:

1. A machine learning method of learning of a second neural network for performing a task of second class classification including a different class from first class classification using a first neural network that is a learned hierarchical neural network which has learned the task of performing the first class classification by machine learning, the method comprising:

a step of adding a new feature amount to at least one intermediate layer included in the first neural network;

a step of generating the second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and a step of causing the second neural network to acquire a processing function of performing the second class classification by performing learning of the second neural network using a set of learning data in which an answer label corresponding to the second class classification is assigned.

2. A machine learning method comprising:
a step of causing a first neural network that is a hierarchical neural network to acquire a processing function of performing first class classification by performing first machine learning regarding the first neural network using a first learning data set in which an answer label corresponding to the first class classification is assigned;
a step of adding a new feature amount to at least one intermediate layer included in the learned first neural network that has acquired the processing function of performing the first class classification;
a step of generating a second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and
a step of causing the second neural network to acquire a processing function of performing second class classification by performing second machine learning regarding the second neural network using a second learning data set in which an answer label corresponding to the second class classification including a different class from the first class classification is assigned.

3. The machine learning method according to claim 1, wherein in a case of learning of the second neural network, a parameter of the calculation path of the existing feature amount present in the learned first neural network is set to be invariable.

4. The machine learning method according to claim 2, wherein in a case of learning of the second neural network, a parameter of the calculation path of the existing feature amount present in the learned first neural network is set to be invariable.

5. The machine learning method according to claim 1, wherein the first neural network has a network structure in which a downsampling network functioning as an encoder and an upsampling network functioning as a decoder are combined, and
the new feature amount is added to the upsampling network out of the downsampling network and the upsampling network.

6. The machine learning method according to claim 2, wherein the first neural network has a network structure in which a downsampling network functioning as an encoder and an upsampling network functioning as a decoder are combined, and
the new feature amount is added to the upsampling network out of the downsampling network and the upsampling network.

7. The machine learning method according to claim 5, wherein the first neural network has a U-Net structure.

8. The machine learning method according to claim 6, wherein the first neural network has a U-Net structure.

9. A learned model having acquired a processing function of performing tasks of first class classification and second class classification through learning of the second neural network by performing the machine learning method according to claim 1.

10. A learned model having acquired a processing function of performing tasks of first class classification and second class classification through learning of the second neural network by performing the machine learning method according to claim 2.

11. A discrimination apparatus comprising:
a learned model having acquired a processing function of performing tasks of first class classification and second class classification through learning of the second neural network by performing the machine learning method according to claim 1.

12. A discrimination apparatus comprising:
a learned model having acquired a processing function of performing tasks of first class classification and second class classification through learning of the second neural network by performing the machine learning method according to claim 2.

13. A non-transitory computer readable storage medium having stored thereon computer commands that, when executed by a computer, cause the computer to:
in machine learning of a second neural network for performing a task of second class classification including a different class from first class classification using a first neural network that is a learned hierarchical neural network which has learned the task of performing the first class classification by machine learning,
add a new feature amount to at least one intermediate layer included in the first neural network;
generate the second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and
cause the second neural network to acquire a processing function of performing the second class classification by performing learning of the second neural network using a set of learning data in which an answer label corresponding to the second class classification is assigned.

14. A non-transitory computer readable storage medium having stored thereon computer commands that, when executed by a computer, cause the computer to:
cause a first neural network that is a hierarchical neural network to acquire a processing function of performing first class classification by performing first machine learning regarding the first neural network using a first learning data set in which an answer label corresponding to the first class classification is assigned;
add a new feature amount to at least one intermediate layer included in the learned first neural network that has acquired the processing function of performing the first class classification;
generate a second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and cause the second neural network to acquire a processing function of performing second class classification by performing second machine learning regarding the second neural network using a second learning data set in which an answer label corresponding to the second class classification including a different class from the first class classification is assigned.

15. A machine learning apparatus performing learning of a second neural network for performing a task of second class classification including a different class from first class classification using a first neural network that is a learned hierarchical neural network which has learned the task of performing the first class classification by machine learning, the apparatus comprising:

a feature amount addition processing unit that adds a new feature amount to at least one intermediate layer included in the first neural network;

a network generation unit that generates the second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and a learning processing unit that causes the second neural network to acquire a processing function of performing the second class classification by performing learning of the second neural network using a set of learning data in which an answer label corresponding to the second class classification is assigned.

16. A machine learning apparatus comprising:

a first learning processing unit that causes a first neural network which is a hierarchical neural network to acquire a processing function of performing first class classification by performing first machine learning regarding the first neural network using a first learning data set in which an answer label corresponding to the first class classification is assigned;

a feature amount addition processing unit that adds a new feature amount to at least one intermediate layer included in the learned first neural network which has acquired the processing function of performing the first class classification;

a network generation unit that generates a second neural network having a structure for maintaining a structure of the first neural network without connecting the new feature amount with respect to a calculation path of an existing feature amount present in the first neural network and within a calculation path of the new feature amount, calculating a new feature amount to be added in a subsequent layer following the layer from which the new feature amount is added, by performing processing of convolving each of the existing feature amount and the new feature amount; and a second learning processing unit that causes the second neural network to acquire a processing function of performing second class classification by performing second machine learning regarding the second neural network using a second learning data set in which an answer label corresponding to the second class classification including a different class from the first class classification is assigned.

* * * * *